US012667290B1

(12) United States Patent
Brody

(10) Patent No.: US 12,667,290 B1
(45) Date of Patent: Jun. 30, 2026

(54) URODYNAMIC STUDY SUBTRACTION CHANNEL USING ABDOMINAL ELECTRICAL ACTIVITY

(71) Applicant: SRS Medical Systems, LLC, North Billerica, MA (US)

(72) Inventor: Lee Brody, Somerville, MA (US)

(73) Assignee: SRS Medical Systems, LLC, Chelmsford, MA (US)

( * ) Notice: Subject to any disclaimer, the term of this patent is extended or adjusted under 35 U.S.C. 154(b) by 603 days.

(21) Appl. No.: 18/113,644

(22) Filed: Feb. 24, 2023

Related U.S. Application Data

(60) Provisional application No. 63/313,787, filed on Feb. 25, 2022.

(51) Int. Cl.
*A61B 5/20* (2006.01)
*A61B 5/00* (2006.01)
*A61B 5/391* (2021.01)
*A61B 5/397* (2021.01)

(52) U.S. Cl.
CPC .............. *A61B 5/205* (2013.01); *A61B 5/391* (2021.01); *A61B 5/397* (2021.01); *A61B 5/6852* (2013.01); *A61B 2560/0223* (2013.01)

(58) Field of Classification Search
CPC ......... A61B 5/205; A61B 5/391; A61B 5/397; A61B 5/6852; A61B 2560/0223
See application file for complete search history.

(56) References Cited

U.S. PATENT DOCUMENTS

| | | | |
|---|---|---|---|
| 2003/0100930 A1* | 5/2003 | Cohen .................... | A61B 5/205 607/40 |
| 2008/0300650 A1* | 12/2008 | Gerber .................... | A61B 5/202 600/300 |
| 2009/0192449 A1* | 7/2009 | Boyden .................... | A61B 5/07 604/65 |
| 2010/0121161 A1* | 5/2010 | Robertson ............ | A61B 5/6874 600/302 |

(Continued)

FOREIGN PATENT DOCUMENTS

| | | | | |
|---|---|---|---|---|
| WO | WO-2010075277 A1 * | 7/2010 | ............. | A61B 5/202 |
| WO | WO-2012103108 A1 * | 8/2012 | ........... | A61B 8/5223 |
| WO | WO-2015125110 A1 * | 8/2015 | ............. | A61B 5/202 |

OTHER PUBLICATIONS

SRS Medical website for purchasing EASTPROTM4, available Dec. 13, 2019 and accessed Feb. 11, 2026 via internet archive wayback machine, https://web.archive.org/web/20191213220407/ https://www.srsmedical.com/complementary-products/ (Year: 2019).*

*Primary Examiner* — Jeffrey G. Hoekstra
(74) *Attorney, Agent, or Firm* — Dicke, Billig & Czaja, PLLC

(57) ABSTRACT

An improved urodynamic study system for generating an abdominal pressure from a measurement of vesical pressure and a measurement of electrical activity of abdominal muscles using electromyography is provided. The system is characterized by a vesical catheter adapted or otherwise equipped to sense vesical pressure, an abdominal electromyography sensor or sensor array to sense electrical activity of abdominal muscles, and, a signal processing interface for producing synchronous channels of vesical pressure and generated abdominal pressure in furtherance of performing a urodynamic patient assessment.

10 Claims, 21 Drawing Sheets

(56)          References Cited

U.S. PATENT DOCUMENTS

| | | | |
|---|---|---|---|
| 2010/0137736 A1* | 6/2010 | Addington | G16H 40/63 |
| | | | 600/561 |
| 2010/0137737 A1* | 6/2010 | Addington | A61B 5/205 |
| | | | 600/561 |
| 2011/0040157 A1* | 2/2011 | Addington | A61M 25/0108 |
| | | | 600/301 |
| 2011/0040211 A1* | 2/2011 | Addington | A61B 5/7475 |
| | | | 600/587 |
| 2011/0046653 A1* | 2/2011 | Addington | A61B 5/6853 |
| | | | 606/196 |
| 2013/0046150 A1* | 2/2013 | Devanaboyina | A61B 5/369 |
| | | | 600/382 |
| 2015/0257695 A1* | 9/2015 | Addington | A61B 5/6853 |
| | | | 600/301 |
| 2017/0055874 A1 | 3/2017 | Papirov et al. | |
| 2019/0216401 A1* | 7/2019 | Brody | A61M 25/10185 |

* cited by examiner

URODYNAMIC STUDY SUBTRACTION CHANNEL USING ABDOMINAL ELECTRICAL ACTIVITY

This is a United States patent application filed pursuant to 35 USC § 111(a) claiming priority under 35 U.S.C. § 120 to U.S. Pat. Appl. Ser. No. 63/313,787 filed Feb. 25, 2022 pursuant to 35 U.S.C. § 111(b) and entitled UDS SUB-TRACTION CHANNEL USING ABDOMINAL EMG, said application incorporated herein by reference in its entirety.

TECHNICAL FIELD

The present disclosure is generally directed to urodynamics studies (UDS), more particularly, improved and/or enhanced UDS wherein either/both of a complex cystometrogram (CMG) and a complex voiding pressure study (VPS) are performed without resort to use of an abdominal catheter in furtherance of determining abdominal pressure values attendant to a void, more particularly still, systems and methods of obtaining detrusor pressure values from measurements of bladder pressure and abdominal electrical activity are provided.

BACKGROUND

UDS is the gold standard diagnostic testing for a variety of lower urinary tract symptoms (LUTS). UDS testing involves the recording of pressures within the body during the bladder filling (i.e., CMG) and/or during the bladder emptying (i.e., VPS). Currently, UDS testing involves placing two separate catheters in the body: (a) a vesical catheter is deployed into the bladder via the urethra, and (b) an abdominal catheter is deployed into the abdominal cavity via the rectum, or via the vagina.

As the bladder fills and empties, the pressure within the bladder undergoes changes. The detection and interpretation of these changing pressures provide important diagnostic information as to the causes of various LUTS. For instance, in the case of a patient who suffers from urge incontinence, can we detect uninhibited detrusor contractions immediately preceding urine leaks? In another clinical example of a patient who suffers from urinary retention, can we detect hypocontractility of the detrusor muscle during a void?

The pressure detected in the bladder (i.e., vesical) is known as Pves. The pressure measured as Pves is generated from (i.e., originates from) one or both of two pressure sources: (a) Pdet: a bladder wall contraction (i.e., a detrusor contraction, namely, a detrusor *urinae* muscle, muscularis propria of the urinary bladder, contraction) which may be a voiding contraction or an uninhibited bladder contraction, and (b) Pabd: a pressure generated in the abdominal cavity which may be induced from a variety of activities such as a cough, sneeze or bearing down.

If one only measures Pves by placing a single sensor in the bladder, s/he does not know the relative contributions of Pabd and Pdet. Therefore, in complex UDS measurements, Pves is detected by placing one pressure sensing catheter in the bladder, and Pabd is independently detect by placing a second pressure sensing catheter in the abdominal cavity. Pdet is a derived value, calculated as follows: Pdet=Pves−Pabd.

FIG. 1 depicts representative UDS results from a complex CMG. Pves and Pabd are measured directly by individual/distinct pressure sensing catheters as a function of time (second and third plots, respectively, from figure top), and Pdet, a calculated or derived value, is plotted there below.

The detecting of Pabd is not without complication. The presence of a second catheter in the rectum has been shown to cause vasovagal syncope. The rectal placement can over-stimulate the vagus nerve, causing vasodilation, and affect the pressure flow relationship in unpredictable ways. In younger benign prostatic hyperplasia (BPH) patients with strong vasovagal responses, the rectal catheter placement is known to result is patient loss of consciousness. Aside from the measurement error caused by the unpredictable vasovagal response, the second catheter placed in the abdominal cavity causes increased testing costs, complications and thusly reduce clinical utilization of this diagnostic.

In order to estimate Pabd, it is believed that a surface electromyography (EMG) measurement can be advantageously made by placing EMG electrodes on the abdomen to sense/sense and measure abdominal activity in lieu of direct measurement of Pabd via an indwelling sensor/detector. Surface EMG is the bioelectric signal measured on the surface of the skin when skeletal muscles contract. A surface EMG electrode placed on the abdomen is intended to detect abdominal contractions. Contrary to alternate extracorporeal detecting/sensing, the subject approach is believed to offer significant clinical and diagnostic advantages.

In light of the foregoing, Applicant SRS Medical Systems, LLC (SRS) contemplates a system/process, and attendant methodology, to create a near real-time Pabd channel by simultaneously detecting Pves and abdominal EMG (AEMG). Preferred topology is a signal processing interface box characterized by two inputs, namely, Pves and AEMG, and two outputs, namely, Pves, and synthesized or generated Pabd. The Pabd generation will be in near real-time, and any value generation delay will also be reflected in an identical delay of the Pves output so that the two signals remain synchronous.

SUMMARY OF THE INVENTION

Notionally, systems devices and methods are provided. As to the contemplated system, namely, an improved urodynamic study system for generating an abdominal pressure from a measurement of vesical pressure and a measurement of electrical activity of abdominal muscles using electromyography, it is generally characterized by a vesical catheter adapted or otherwise equipped to sense vesical pressure, an abdominal electromyography sensor or sensor array to sense electrical activity of abdominal muscles, and, a signal processing interface for producing synchronous channels of vesical pressure and generated abdominal pressure in furtherance of performing a urodynamic patient assessment.

An advantageous, non-limiting signal processing interface notionally includes signal receiver modules, a processor for calibrating select signal from the signal receiver modules, and an output device for outputting synchronous channels of measured values of vesical pressure and generated abdominal pressure correlated to the calibrated select signals. The signal receiver modules are configured to receive first and second signals comprised, respectively, of measured values of vesical pressure and measured values of abdominal electrical activity.

Select signals for calibration via the are characterized by first measured values of each of vesical pressure and abdominal electrical activity corresponding to a passive patient status which is characterized by an empty bladder and inactive non-volitional abdominal contractions, and which are further characterized by one or more measured values of abdominal electrical activity corresponding to one or more active volitional abdominal contractions so as to delimit calibrated select signals evidencing a relationship between abdominal electrical activity and abdominal pressure in furtherance of obtaining generated abdominal pressure values.

As to the contemplated device, namely a signal processing interface for producing synchronous channels of vesical pressure and generated abdominal pressure in furtherance of performing a urodynamic patient assessment, it is generally characterized by signal receivers, a processor and an output generator or device. One or more signal receivers are configured to receive first and second signals comprised, respectively, of measured values of vesical pressure and measured values of abdominal electrical activity.

The processer effectuated calibration of select signals from the one or more signal receiver received thereby. The select signals from the one or more signal receiver modules are characterized by first measured values of each of vesical pressure and abdominal electrical activity corresponding to a passive patient status characterized by an empty bladder and inactive non-volitional abdominal contractions. The select signals are further characterized by one or more measured values of abdominal electrical activity corresponding to one or more active volitional abdominal contractions so as to delimit calibrated select signals evidencing a relationship between abdominal electrical activity and abdominal pressure in furtherance of obtaining generated abdominal pressure values. The output generator outputs synchronous channels of measured values of vesical pressure and generated abdominal pressure correlated to the calibrated select signals.

As to the contemplated method, the measurement of vesical pressure and abdominal electrical activity corresponding to a passive patient status characterized by an empty bladder and inactive non-volitional abdominal contractions, first measured values, and to an active patient status characterized by one or more active volitional abdominal contractions, second measured values, is undertaken. Thereafter, data associated with first measured values of each of vesical pressure and abdominal electrical activity, and data associated with second measured values of each of vesical pressure and abdominal electrical activity is comparatively assessed.

Advantageously, the comparative data assessment includes performing a calibration protocol with regard to the second measured values of vesical pressure and abdominal electrical activity corresponding to an active patient status characterized by one or more active volitional abdominal contractions so as to establish a relationship for and between abdominal electrical activity and abdominal pressure.

Via an optional step, determination of signal quality of signals associated with measured values of abdominal electrical activity is undertaken. Do the signals enable generating abdominal pressure values from measured values of abdominal electrical activity during a urodynamic study as a result of the comparative assessment of data associated with first measured values of each of vesical pressure and abdominal electrical activity, and data associated with second measured values of each of vesical pressure and abdominal electrical activity?

In light of having undertaken the comparative assessment, abdominal pressure values are generated or synthesized from measured values of abdominal electrical activity during the urodynamic study in furtherance of a establishing a real-time/near real time abdominal pressure channel having origins in abdominal electrical activity measurements. Alternatively, to optimize the calculations, the establishment of the abdominal pressure channel can occur after a longer delay, and even after the UDS study is complete. Finally, detrusor pressure is derived from vesical pressure and the synthesized abdominal pressure. More specific features and advantages obtained in view of the summarized features will become apparent with reference to the drawing figures and DETAILED DESCRIPTION OF THE INVENTION.

BRIEF DESCRIPTION OF THE DRAWINGS

All figures have been prepared, and are included to facilitate and/or enhance an understanding of the basic teachings of the contemplated embodiments, and/or the concepts underlying same, and are incorporated in and constitute a part of this specification. While the drawings illustrate embodiments and context with respect thereto, and together with the description serve to explain principles of embodiments, other embodiments and many of the intended advantages of the disclosed systems, subsystems, assemblies, subassemblies, apparatus, devices, mechanisms, methods, rubrics, protocols, etc. will be readily appreciated as they become better understood by reference to the following detailed description and figures. It is to be noted, as circumstances warrant, that the elements of the drawings are not necessarily to scale relative to each other, with like reference numerals designating corresponding similar parts/structures.

FIGS. 1-9 are provided herewith wherein:

FIG. 1 illustratively depicts commonplace UDS results, in particular, Pves and Pabd values plotted as a function of time part-and-parcel of a complex CMG;

FIG. 2 schematically illustrates an advantageous, non-limiting signal processing interface for producing synchronous/near synchronous channels of vesical pressure and synthesized abdominal pressure in furtherance of performing a urodynamic patient assessment;

FIG. 3 is a process flow diagram of an enhanced UDS study characterized by an advantageous non-limiting method of synthesizing or generating abdominal pressure values from measured vesical pressure values and measured abdominal electrical activity;

DETAILED DESCRIPTION OF THE INVENTION

In advance of setting out particulars/select particulars for the contemplated system/device and method(s), an overview of the disclosure is hereinafter provided. It is to be noted that the overview is intended as a preview or framework related to Applicant's work and is not to be construed as limiting in any way.

Notionally, synthesis or generation of Pabd, reliably and repeatably, is readily achieved via utilization of a novel, non-limiting signal processing interface (FIG. 2) and/or via practice of a novel, non-limiting calibration protocol for generating or synthesizing abdominal pressure values from measured vesical pressure values and measured abdominal electrical activity part-and parcel of an enhanced UDS study (FIG. 3), or via variants thereof. Illustratively, plotted Pves and AEMG UDS data sets are provided FIGS. 4A-C, in three parts, with zeroed versions of the data sets correspondingly shown FIGS. 5A-C. Thereafter, a calibration protocol, as illustratively depicted in FIGS. 6A-C, 7A-C & 8A-C, each in three parts, leverages a comparative assessment(s) of provocative maneuver portions of the data sets of FIGS. 5A-C and wherein combined Pves AEMG processed data sets supplement the illustrated zeroed data sets of FIGS. 5A-C. Finally, and in light of the assessment and calibration process, synthesized or generated Pabd values replace AEMG data sets, FIGS. 9A-C, with Pves data sets and corresponding derived/calculated Pdet values provided and shown. Hereinafter, the system, method and Pabd synthesis from AEMG is taken up.

Figure 1:
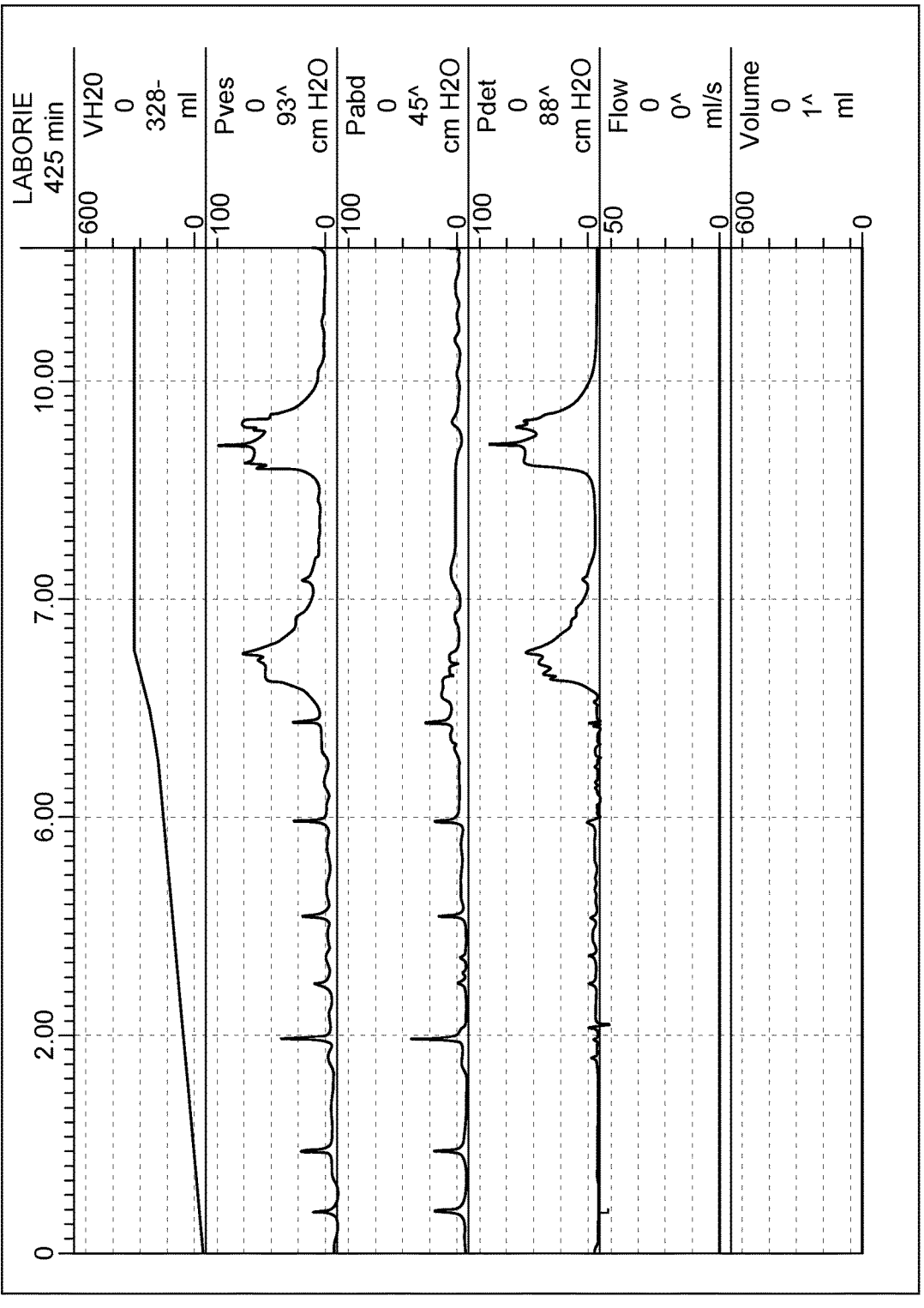
Figure 2:
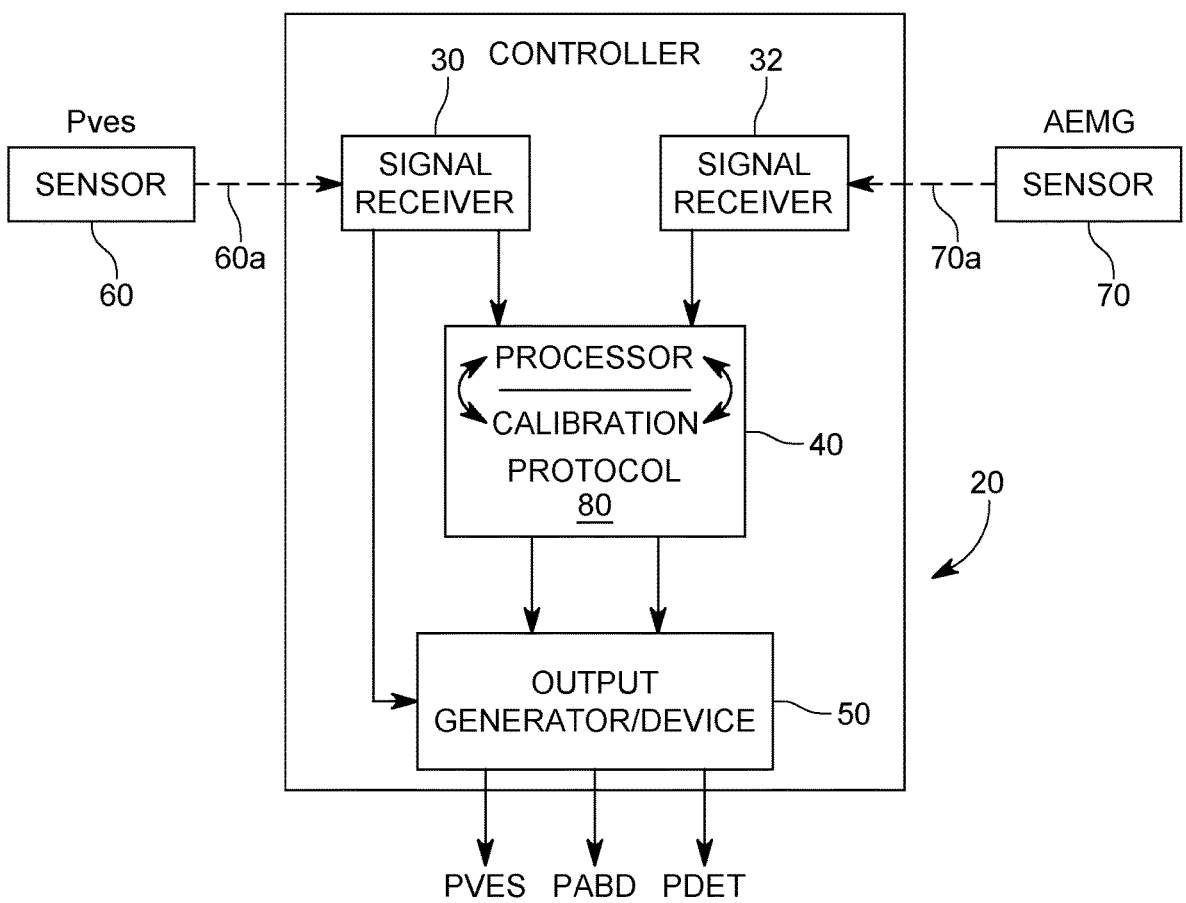

With reference now to FIG. 2, and advantageously, but not necessarily, in the context of a urodynamics test system, e.g., and without limitation, Applicant's EASYPRO™ 4 Urodynamics System, there is schematically shown a signal processing interface 20 for producing synchronous/near synchronous channels of vesical pressure and generated (i.e., synthesized) abdominal pressure in furtherance of performing a urodynamic patient assessment. The signal processing interface, advantageously but not necessarily part-and-parcel of a controller, or in operative combination therewith, is advantageously characterized by one or more signal receivers, 30, 32, a processor 40 and an output generator/device 50. The signal processing interface may be a discrete element operatively united with/to a UDS instrument, or the interface may be integral thereto. Notionally, such systems are further characterized by, among other items, a vesical catheter, adapted or otherwise equipped to sense vesical pressure, and an AEMG sensor or sensor array to sense electrical activity of abdominal muscles, i.e., sensors 60 & 70 respectively.

The signal receivers or modules are configured to receive signals, e.g., first and second signals, comprised, respectively, of measured values of vesical pressure, 60a, and measured values of abdominal muscle electrical activity, 70a. The measured values have origins in attendant elements of the contemplated system (not shown), for example and without limitation, pressure sensor 60 of a vesical catheter and an AEMG sensor array 70.

The processer operates to calibrate select signals received thereby, from the one or more signal receivers, via execution of a calibration protocol 80 advantageously but not necessarily embodied in software directly/indirectly accessed thereby as the case may be. Select signals from the one or more signal receiver modules are characterized by first measured values of each of vesical pressure and abdominal electrical activity corresponding to a passive patient status characterized by an empty bladder and inactive non-volitional abdominal contractions. Moreover, the select signals from the one or more signal receiver modules are further characterized by one or more measured values of abdominal electrical activity corresponding to one or more active volitional abdominal contractions so as to support delimiting calibrated select signals evidencing a relationship between abdominal electrical activity and abdominal pressure in furtherance of obtaining generated abdominal pressure values/synthesizing same.

Finally, the output generator/device 50 outputs synchronous/near synchronous channels of measured values of vesical pressure and generated abdominal pressure correlated to the calibrated select signals. Such devices are well known, with a display screen or display screen/printer combination preferred but not limiting.

Figure 3:
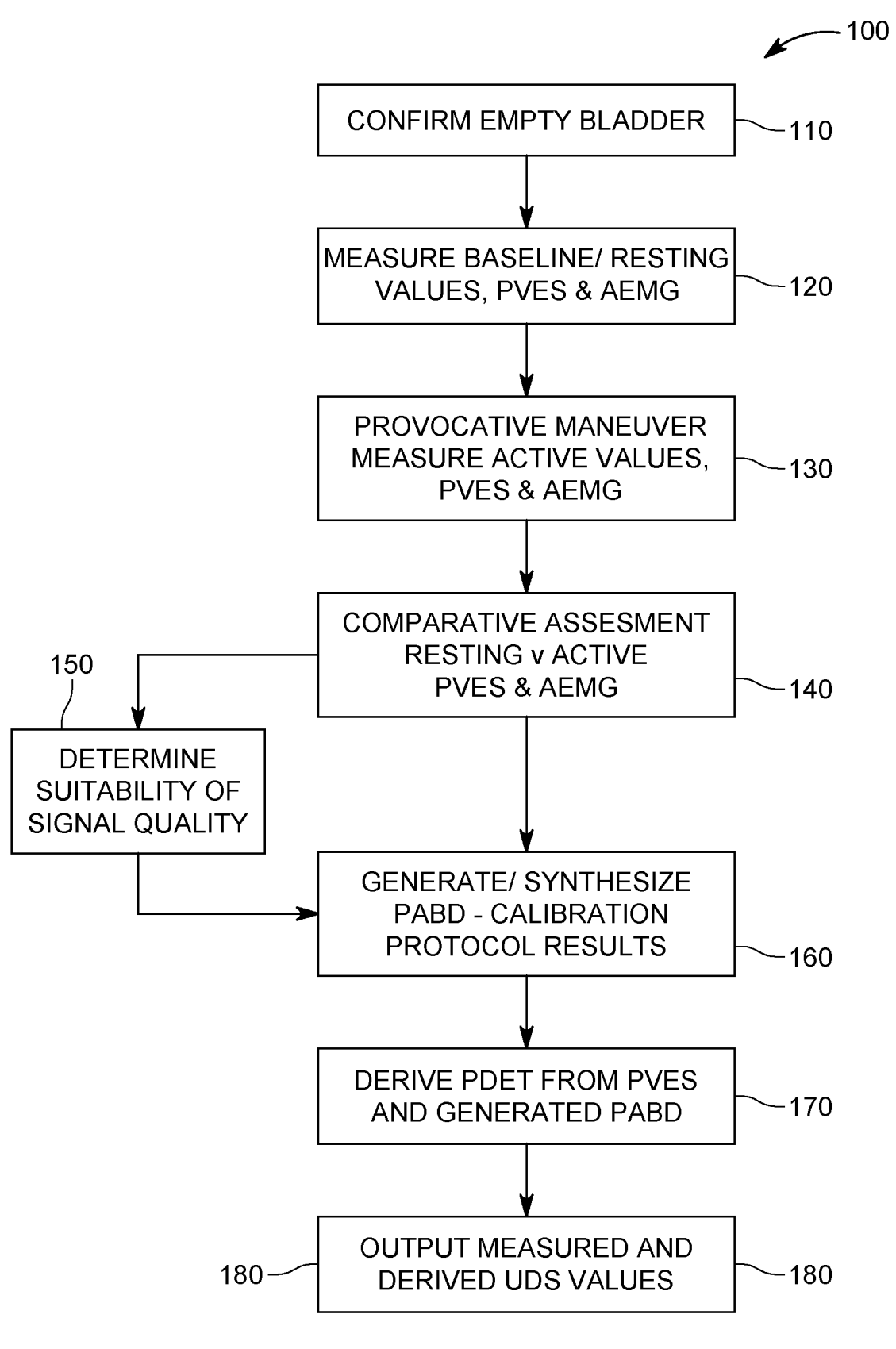

With reference now to FIG. 3, an advantageous non-limiting method 100 is set forth in the form of a process flow diagram. In furtherance of establishing a relationship or relatedness for/between AEMG and Pabd for a particular patient, the contemplated process commences with a confirmation that the patient's bladder is empty at step 110. Initial, baseline values of Pves and abdominal electrical activity (e.g., AEMG), measured values, are thereafter obtained, step 120. Notionally, the baseline values are "resting" values, that is to say, the baseline values correspond to a passive patient status characterized by an empty bladder and inactive non-volitional abdominal contractions.

At step 130, a calibration related step, in connection to a patient instruction to perform a provocative maneuver in furtherance of activating the abdomen and effectuating abdominal pressure, "active" values of Pves and abdominal electrical activity (e.g., AEMG), measured values, are obtained. More particularly, this further or second set of measured values of each of vesical pressure and abdominal electrical activity correspond to an active patient status characterized by one or more active volitional abdominal contractions resulting from the provocative maneuver. A typical provocative maneuver advantageously involves a "cough, cough, push, cough" abdominal activation sequence, however, the contemplated activation need not be so limited.

The measurements made of Pves during this step is reflective of the direct measurement that would be made of Pabd if a second catheter was in place because there was no Pdet response (i.e., component) during this data acquisition period. This can verified by repeating the step/routine in the event that there was an unrelated bladder contraction.

In light of having memorialized data associated with passive/first measured values of each of vesical pressure and abdominal electrical activity, and data associated with active/second measured values of each of vesical pressure and abdominal electrical activity, a calibration protocol, characterized by a comparative assessment, step 140, is undertaken to, initially, and optionally, determine, step 150, the suitability of signal quality of signals associated with measured values of abdominal electrical activity to enable generating abdominal pressure values from measured values of abdominal electrical activity during the UDS study, and ultimately delimit a relationship for, between and among Pves and AEMG as will be subsequently taken up in connection to an illustrative example. Thereafter, having establish a working relationship for the variables, abdominal pressure values are generated or synthesized, step 160, from measured values of abdominal electrical activity during a urodynamic study as a result of the comparative assessment of data associated with first measured values of each of vesical pressure and abdominal electrical activity, and data associated with second measured values of each of vesical pressure and abdominal electrical activity. Finally, Pdet is derived from measured Pves and derived Pabd in step 170, with measured and derived UDS values outputted at step 180.

With general reference now to FIGS. 4A-C-9A-C, exemplary Applicant UDS study findings, reflective of the contemplated methodology and intended to illustrate the calibration protocol utilized in the fabrication of Pabd from AEMG and resultant Pdet derived, are set forth, each in three parts. As to the data sets, namely, Pves and AEMG, units of measure (i.e., magnitudes, y-axis) are centimeters of water (cmH2O) and microvolts (µV) for each respectively, with each value measured/recorded as a function of time, units of measure (i.e., magnitude, x-axis) are tenths of a second.

Figure 4A:
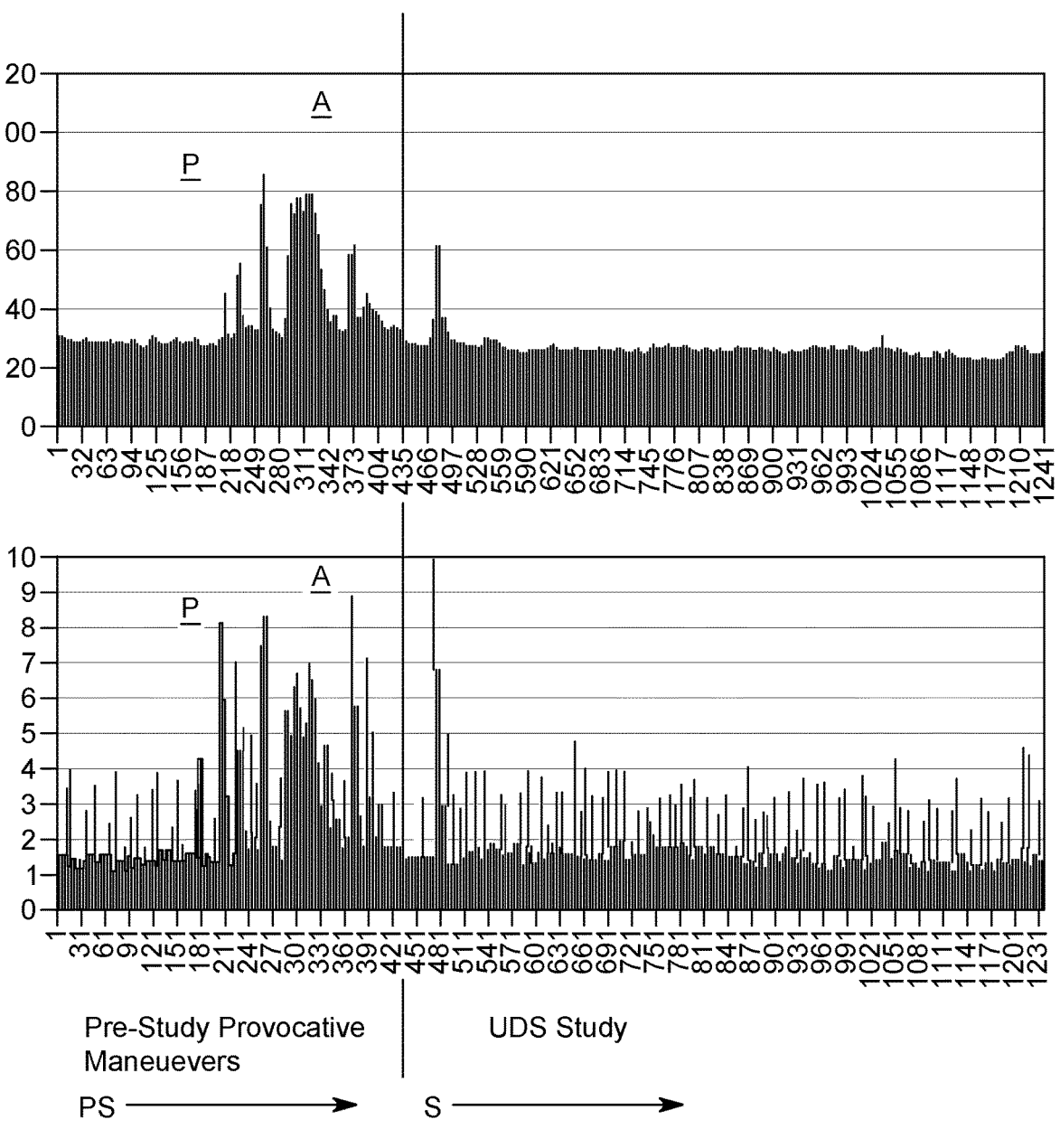
FIGS. 4A-C are an illustrative representation, in three parts, of measured variable values (i.e., data sets), plotted as a function of time for Applicant's enhanced UDS study, more particularly, Pves and AEMG data sets obtained during an enhanced UDS study characterized by the implementation of the FIG. 3 methodology.
Figure 4B:
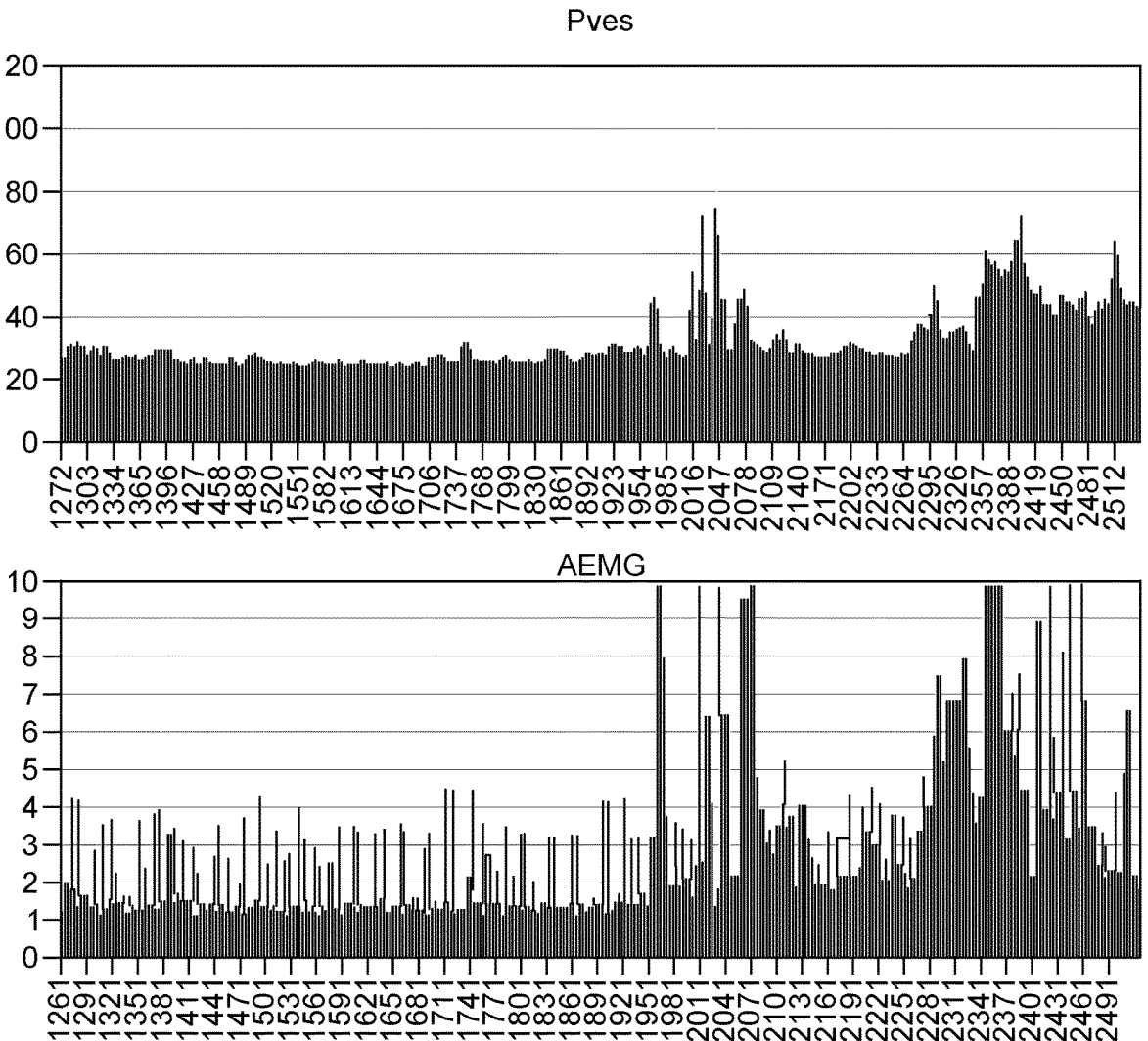
Figure 4C:
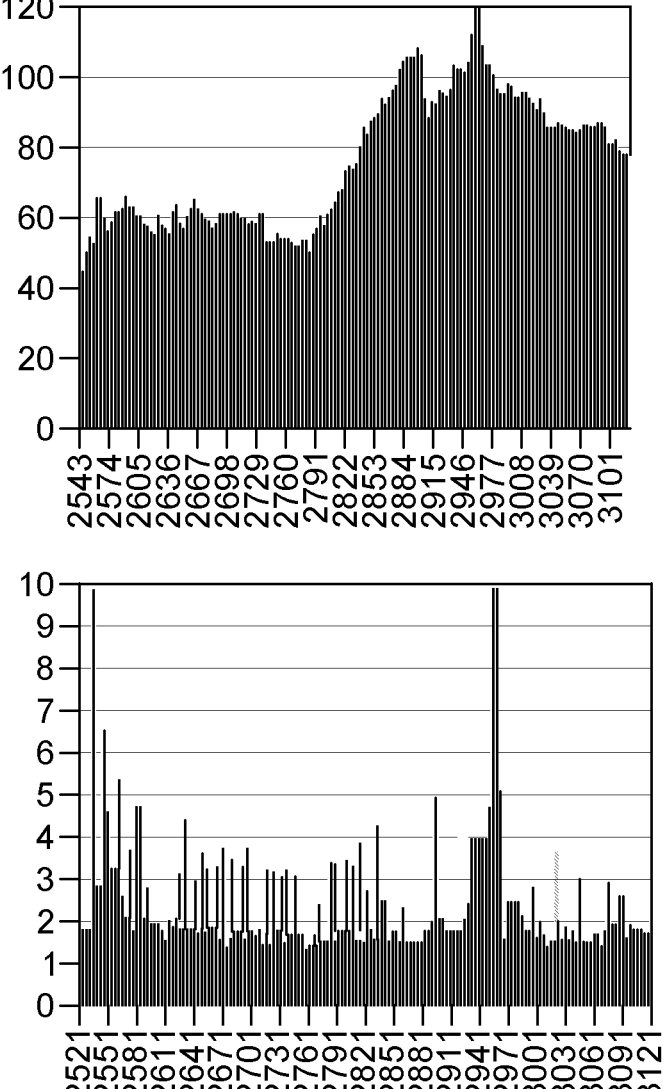

With initial reference to the graphic sequence of FIGS. 4A-C, both pre-study acquired data, PS, and UDS study acquired data, S, are indicated. In keeping with the heretofore set forth methodology, PS comprises measured values of each of vesical pressure and abdominal electrical activity corresponding to a passive patient status, P, characterized by an empty bladder and inactive non-volitional abdominal contractions, and measured values of each of vesical pressure and abdominal electrical activity corresponding to an active patient status, A, characterized by one or more active volitional or intentioned abdominal contractions. As is generally indicated commencing near or at about time marker 200, provocative maneuver values for Pves and AEMG are shown, more particularly, resultant values for each having origins in a cough/cough/push/cough clinician request. Having suitably concluded the provocative maneuver, the UDS commences, as shown, near or about time marker 440.

Once the UDS study starts, the patient has an initial cough (i.e., near or about time marker 480) as is represented, and then the empty bladder is infused with sterile water over an extended period. Generally, the patient will report a first sensation of the bladder filling, and then will subsequently express a desire to void. When the patient has a strong desire to void, bladder filling ends, and the patient prepares to void. In this study, as the patient attempts to void, s/he activates the abdomen to push the urine out, and the detrusor muscle then begins to contract to aid emptying of the bladder (i.e., near or about time marker 1950).

Figure 5A:
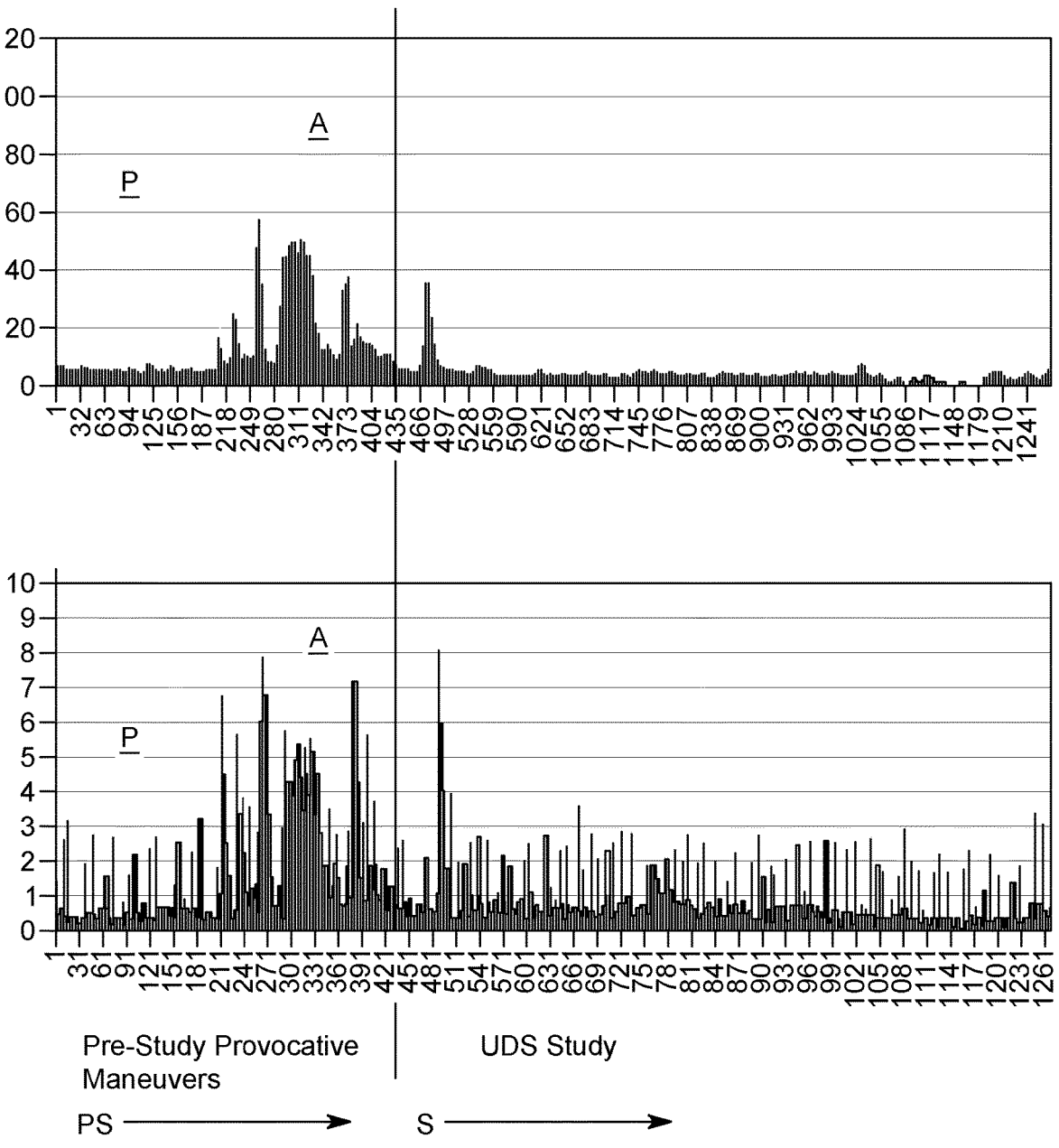
FIGS. 5A-C illustratively represent zeroed variable values of FIGS. 4A-C.
Figure 5B:
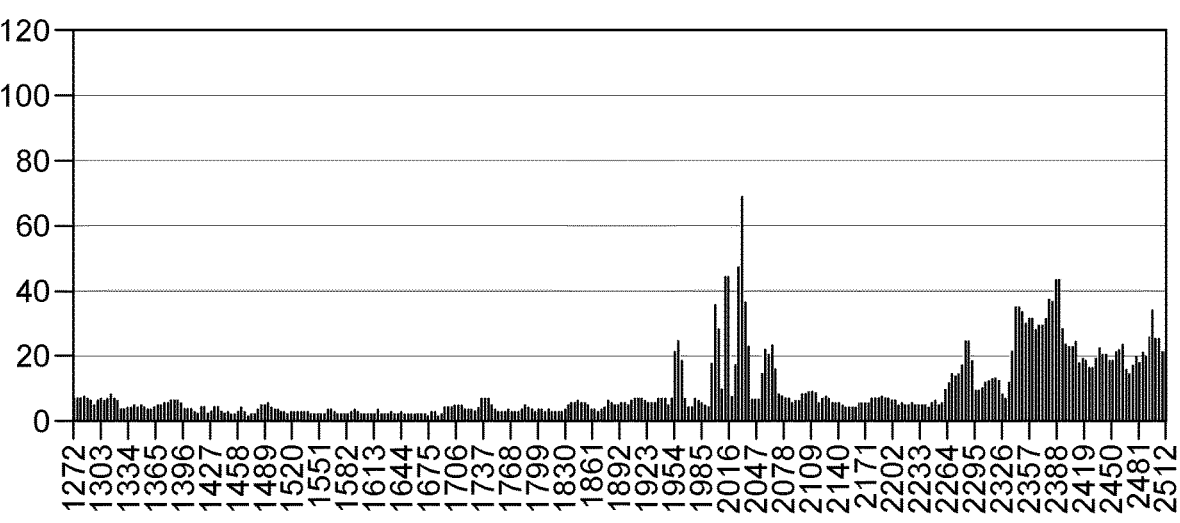
Figure 5B:
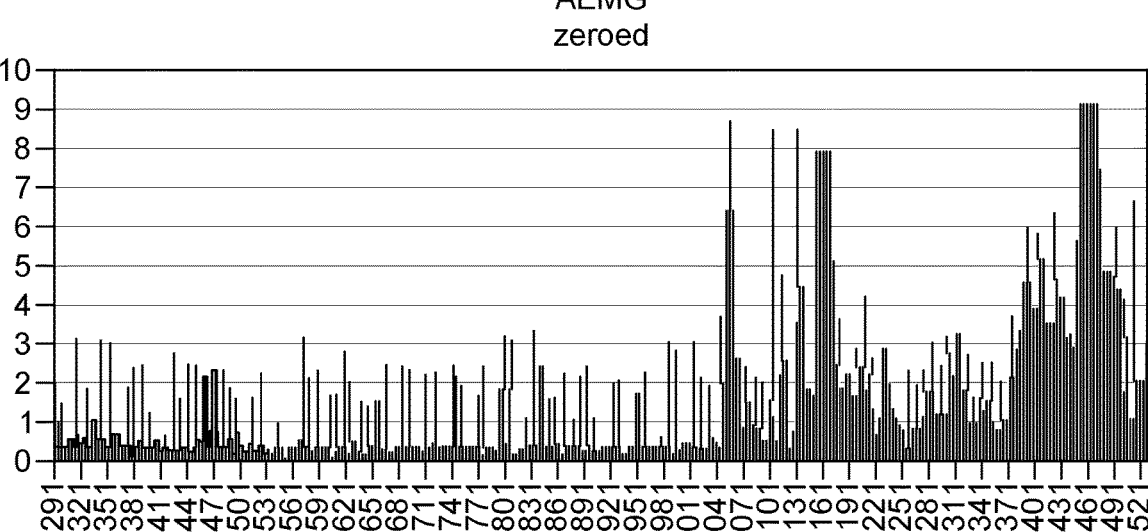
Figure 5C:
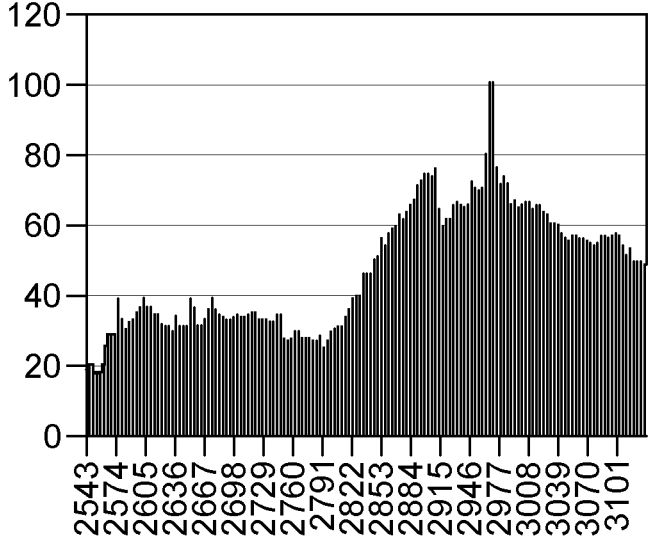
Figure 5C:
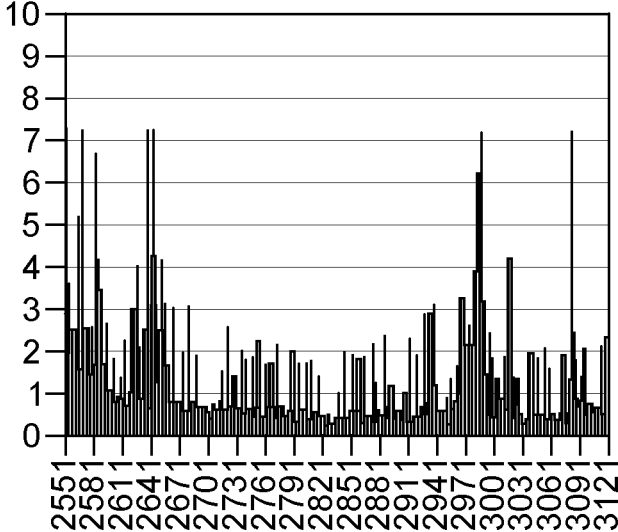

With additional and brief reference now to the graphic sequence of FIGS. 5A-C, and comparison with the graphic sequence of FIGS. 4A-C, the x-axis values for each of the measured variables, Pves and AEMG, are indicated as zeroed values. Essentially, the variable magnitudes of FIGS. 5A-C have been reduced by the corresponding minimum measured value for that variable FIGS. 4A-C (i.e., subtraction of the baseline values of the variables).

Figure 6A:
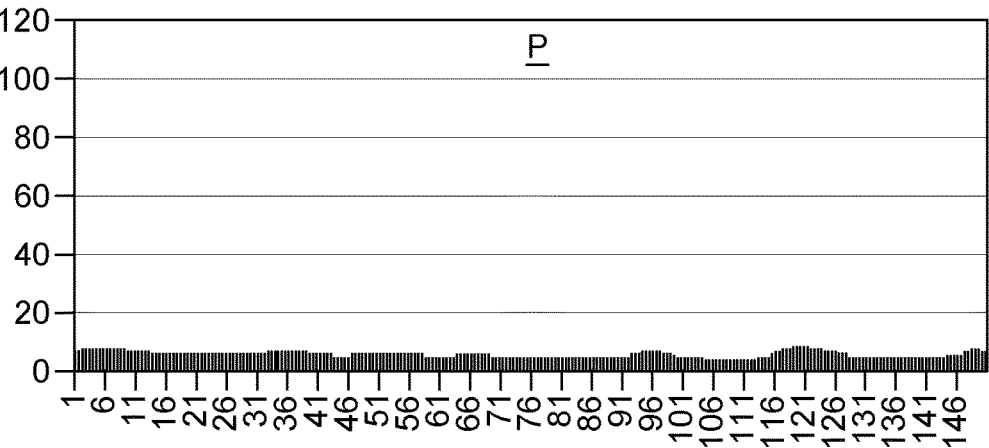
FIGS. 6A-C, 7A-C, & 8A-C each illustratively represent, in three parts, advantageous but not limiting sequential processes/steps of the contemplated calibration protocol integral to step 140 of the FIG. 3 method; and, FIGS. 9A-C illustratively represent, in three parts, synthesized Pabd values, having origins in the calibration protocol processes of FIGS. 6-8, plotted as a function of time, derived values of Pves using the synthesized Pabd values likewise depicted.
Figure 6A:
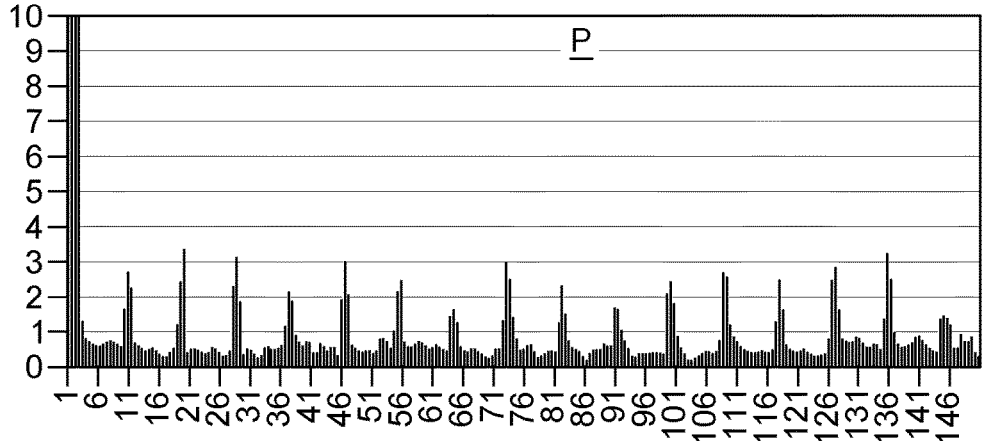
Figure 6A:
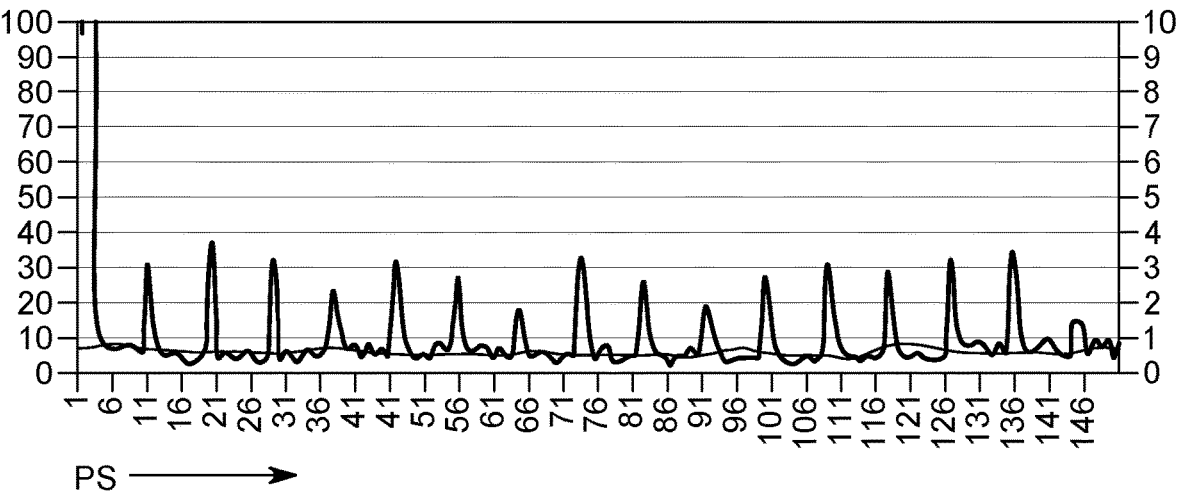
Figure 6B:
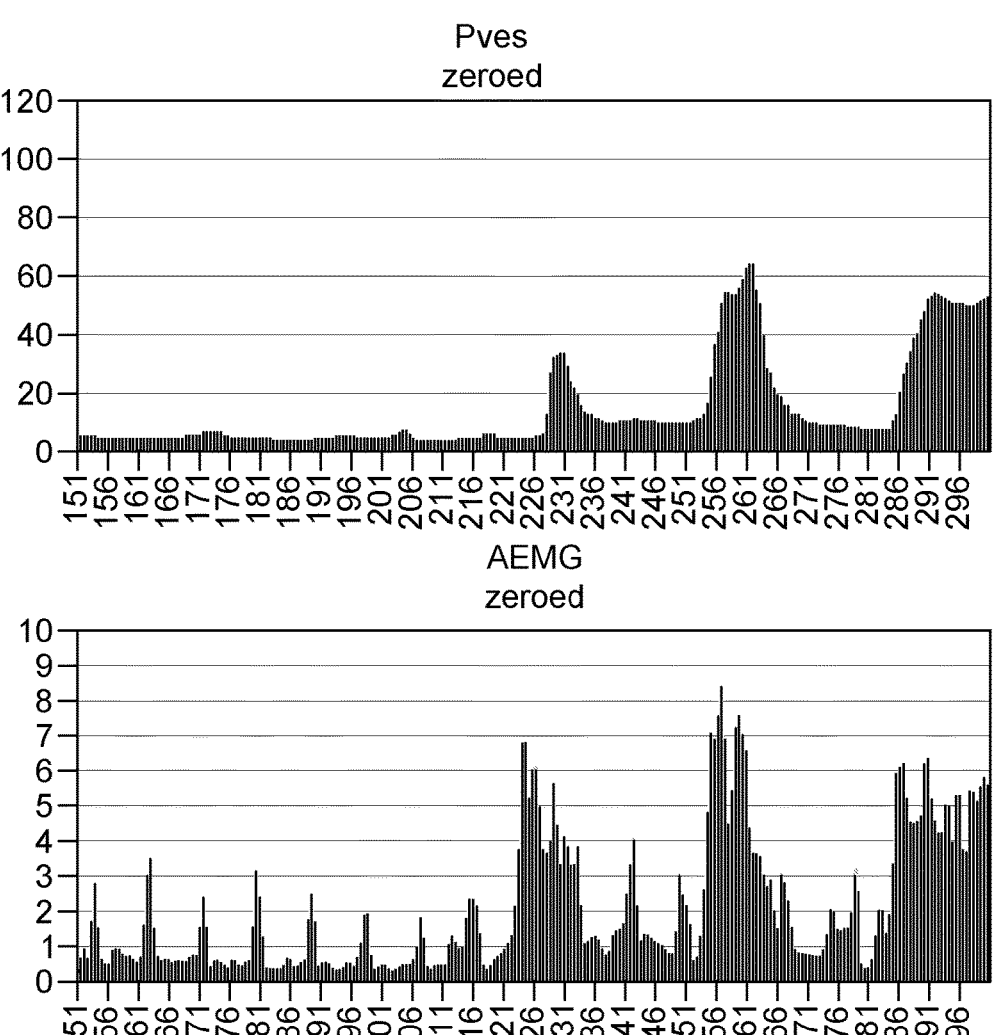
Figure 6B:
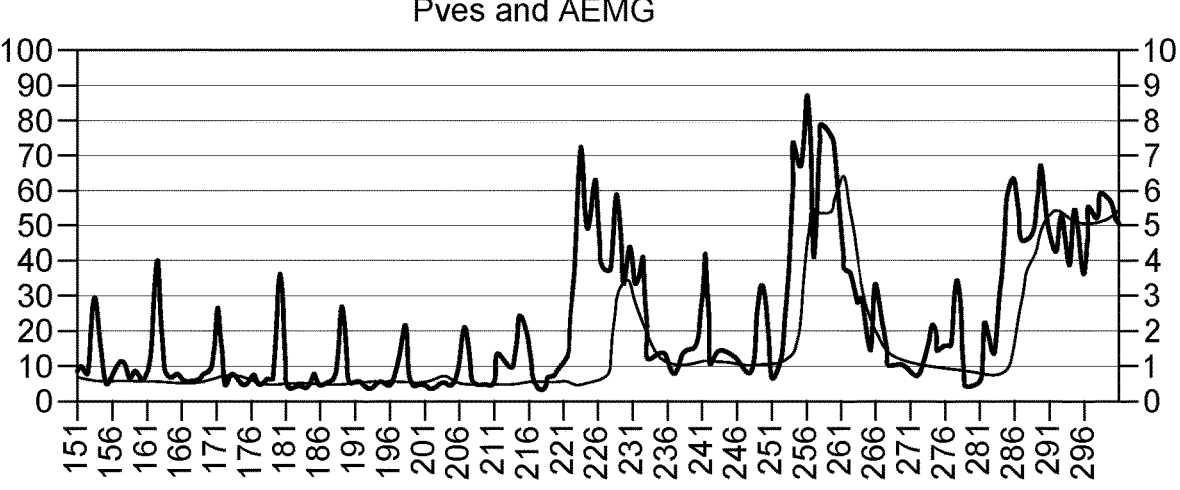
Figure 6C:
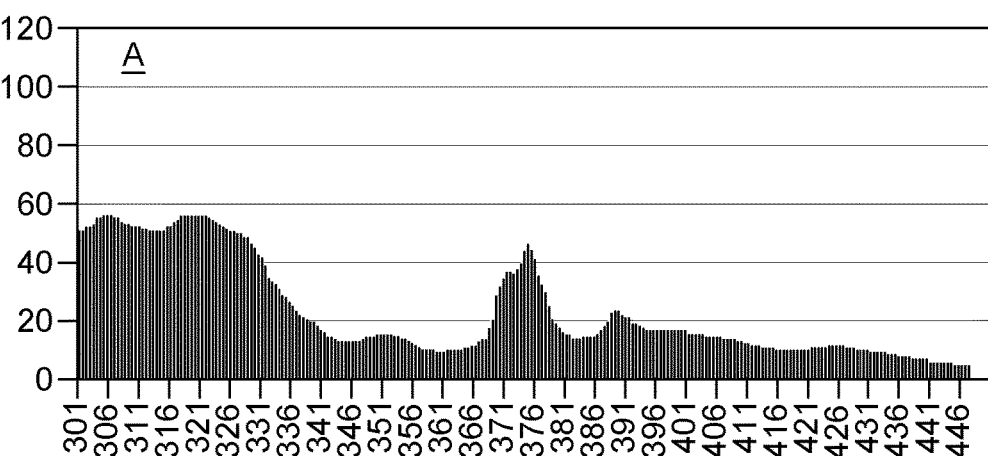
Figure 6C:
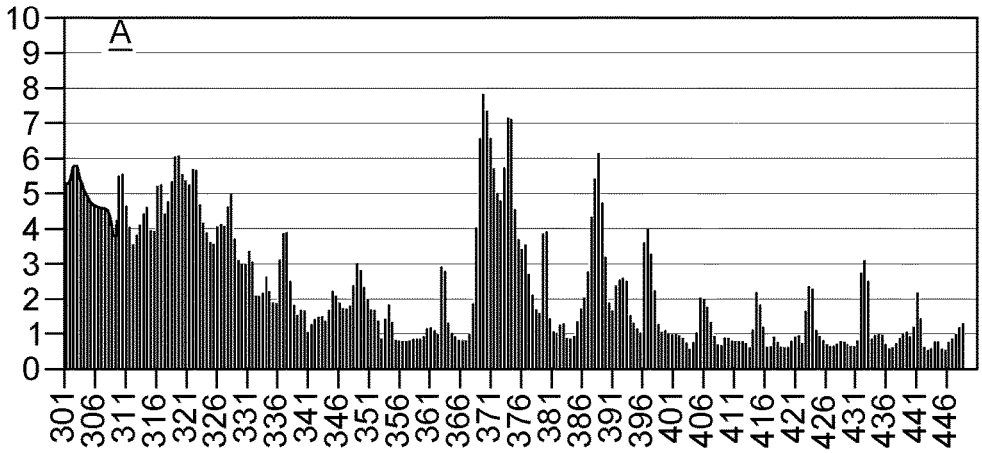
Figure 6C:
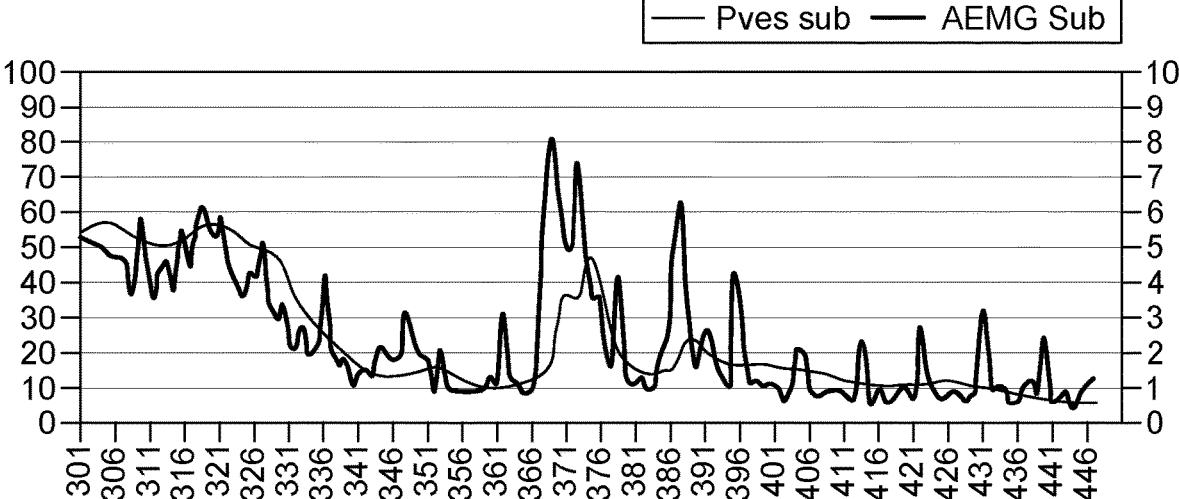
Figure 7A:
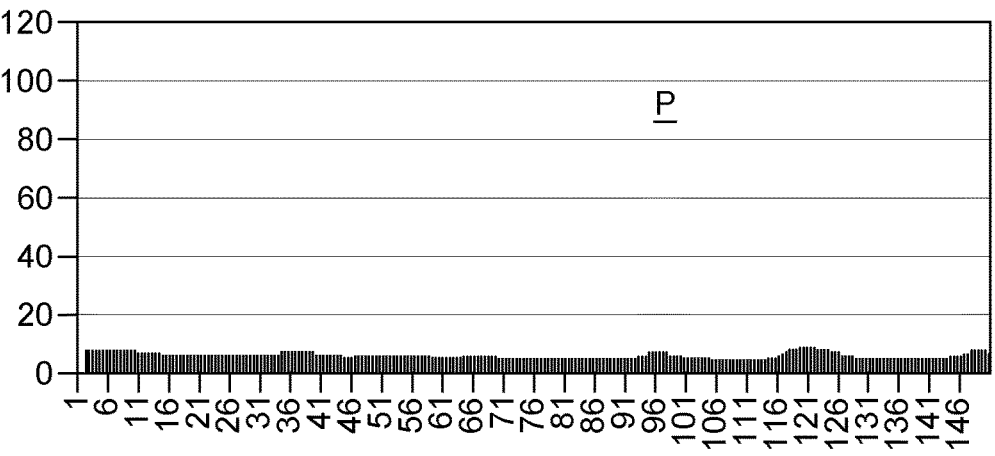
Figure 7A:
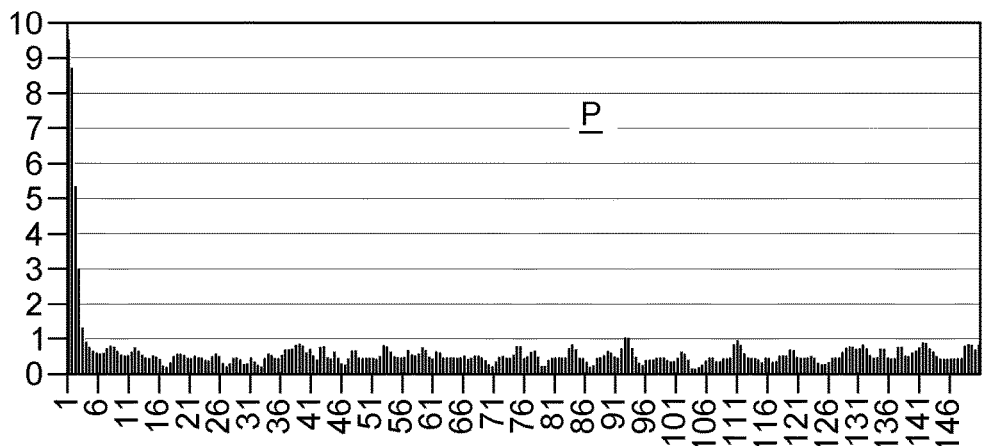
Figure 7A:
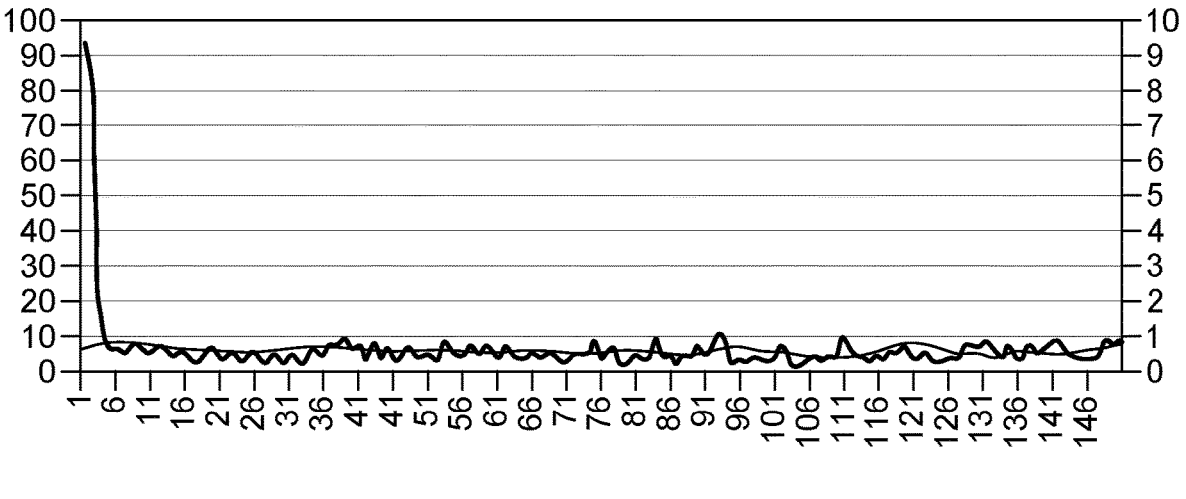
Figure 7B:
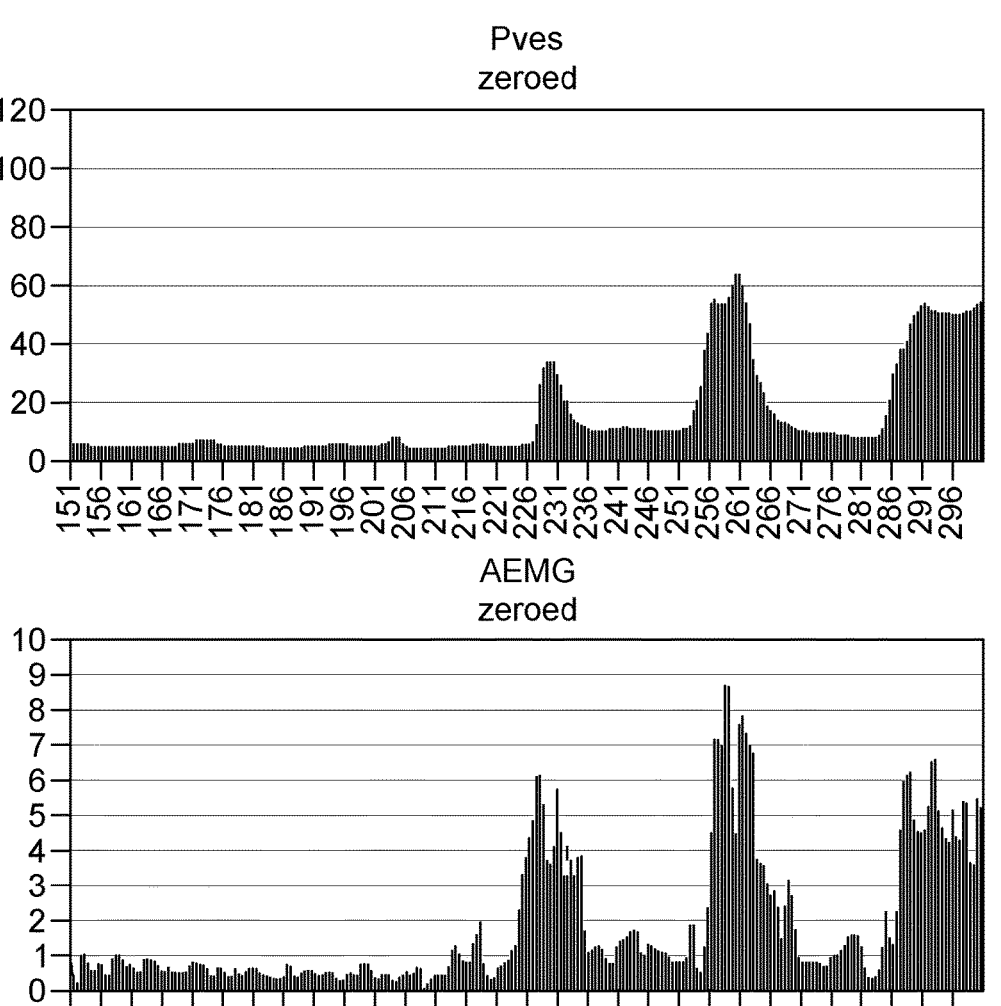
Figure 7B:
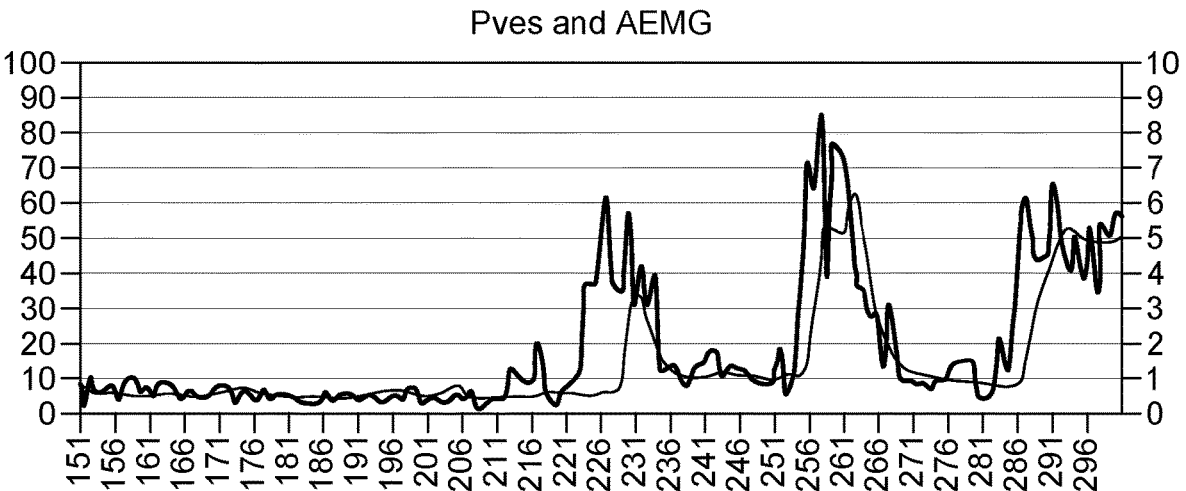
Figure 7C:
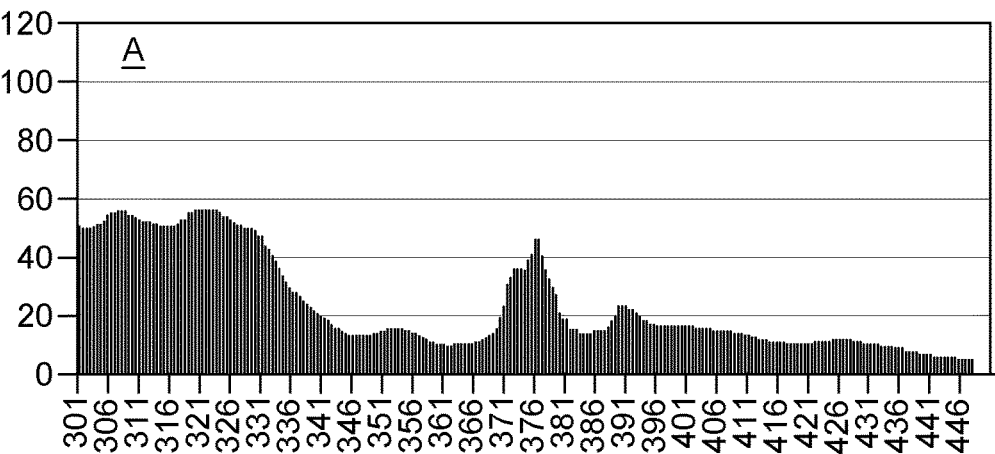
Figure 7C:
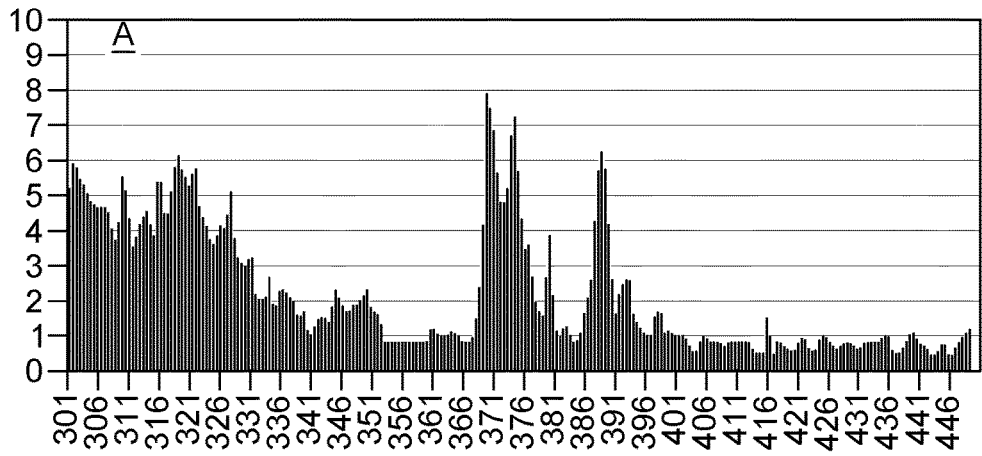
Figure 7C:
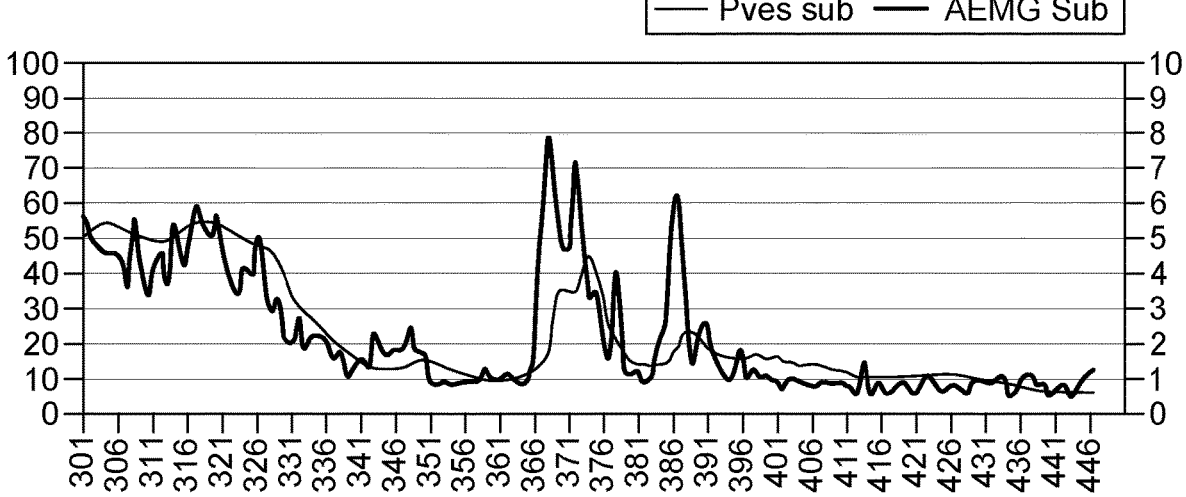
Figure 8A:
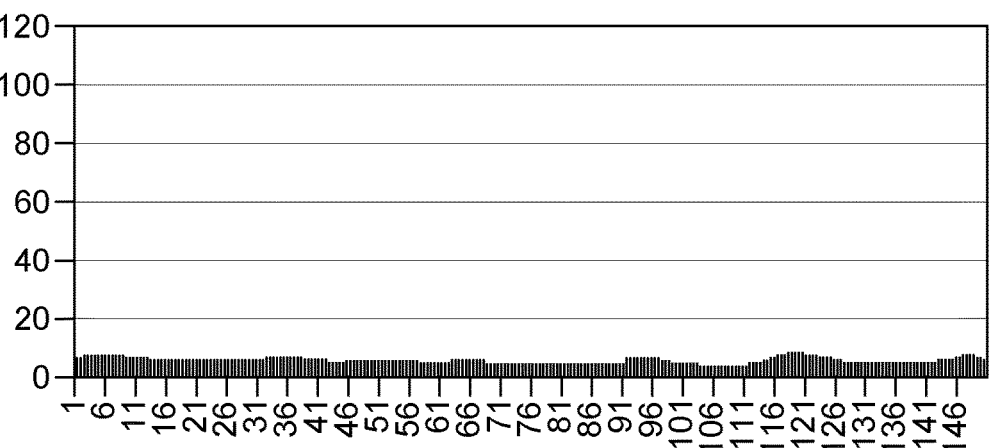
Figure 8A:
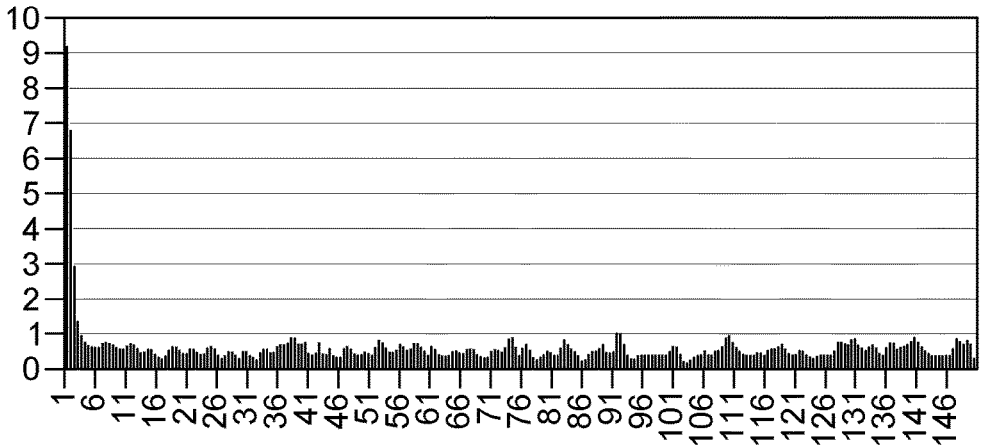
Figure 8A:
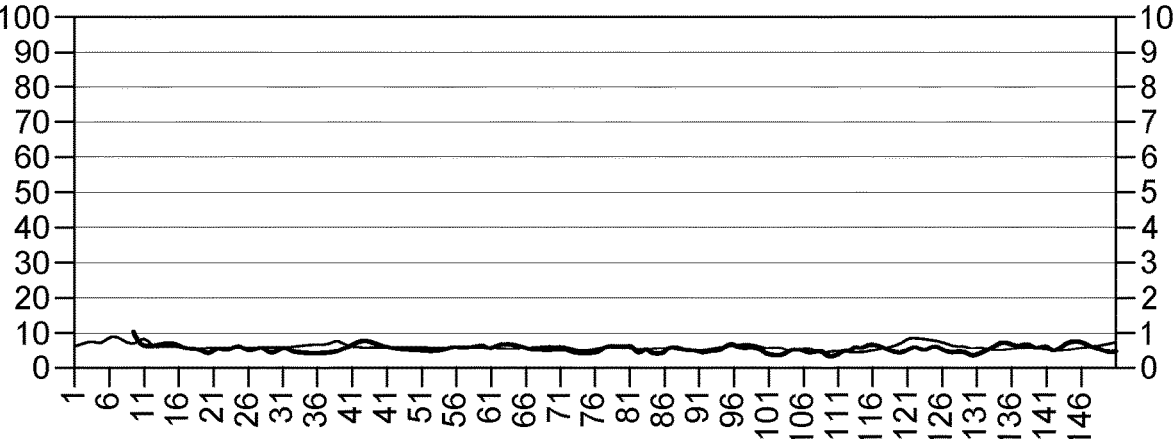
Figure 8B:
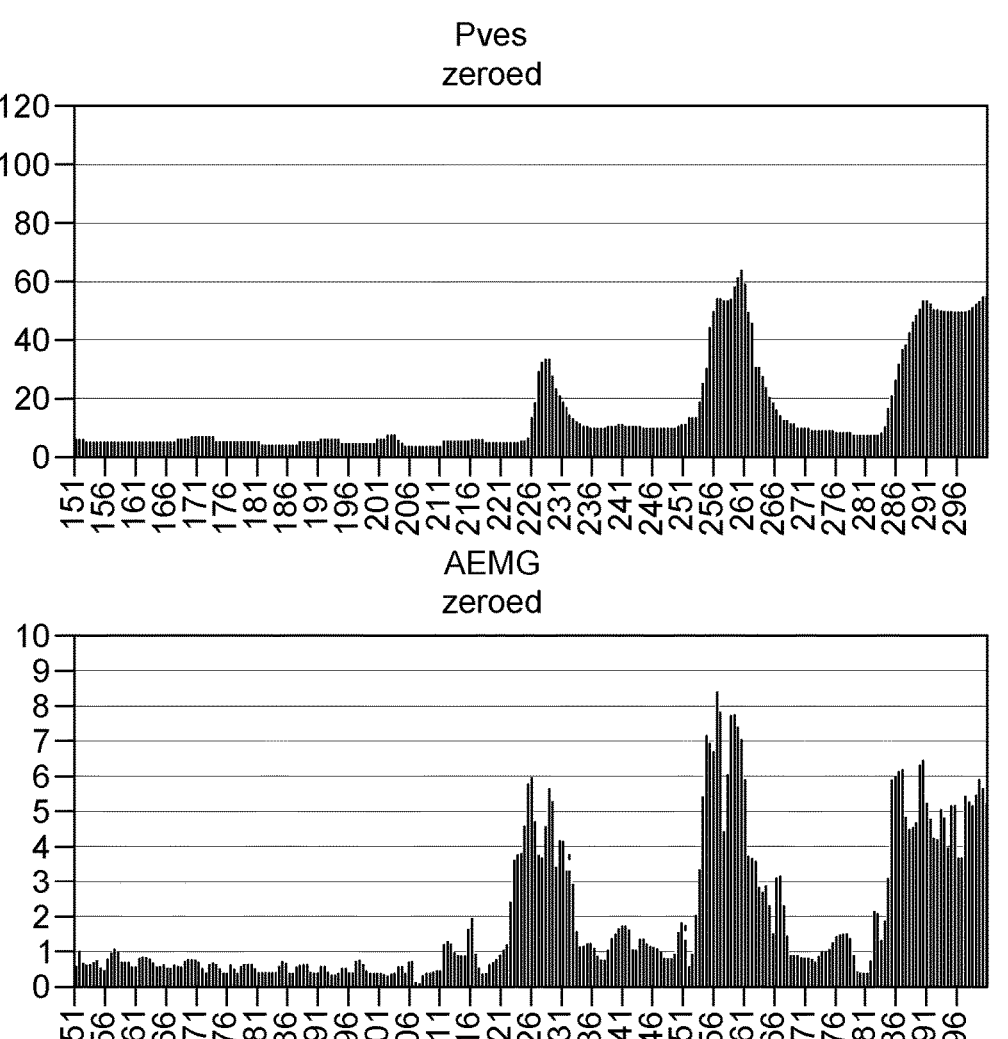
Figure 8B:
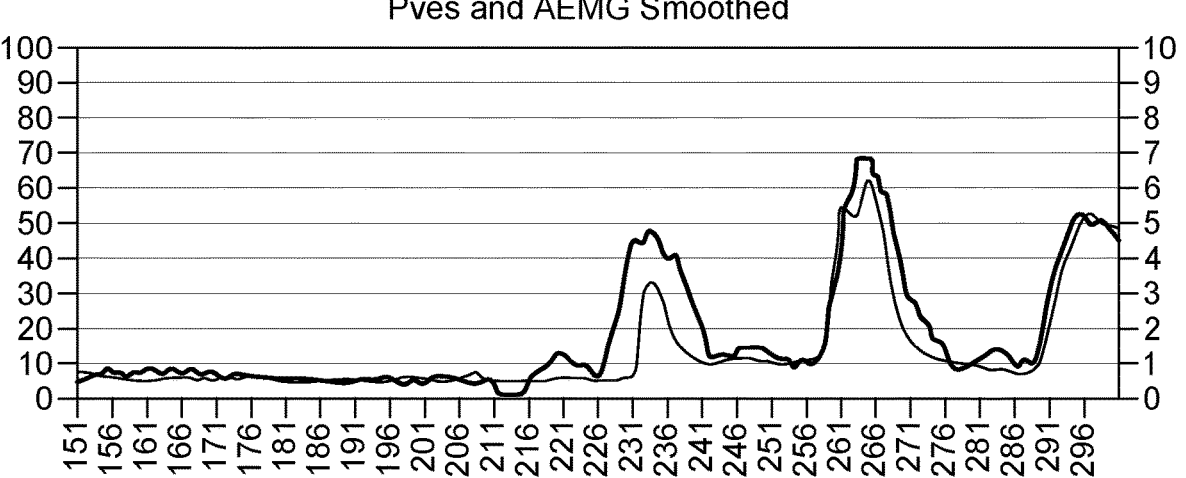
Figure 8C:
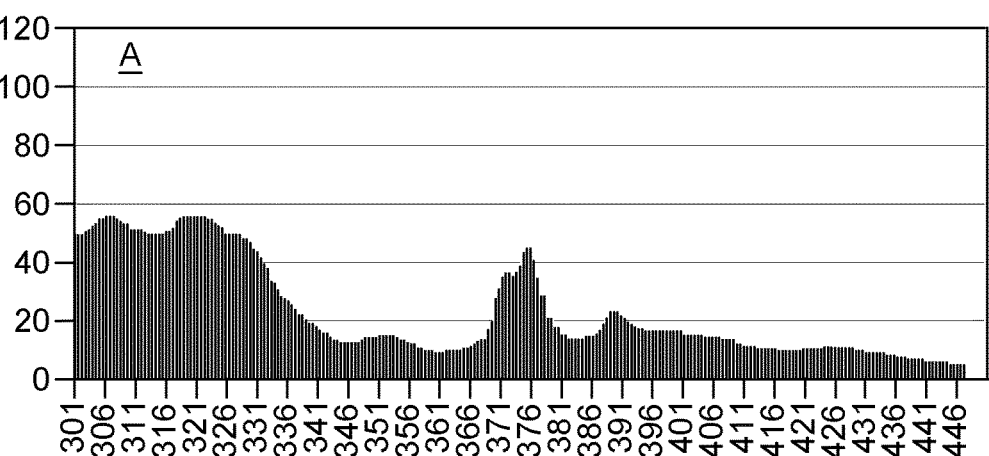
Figure 8C:
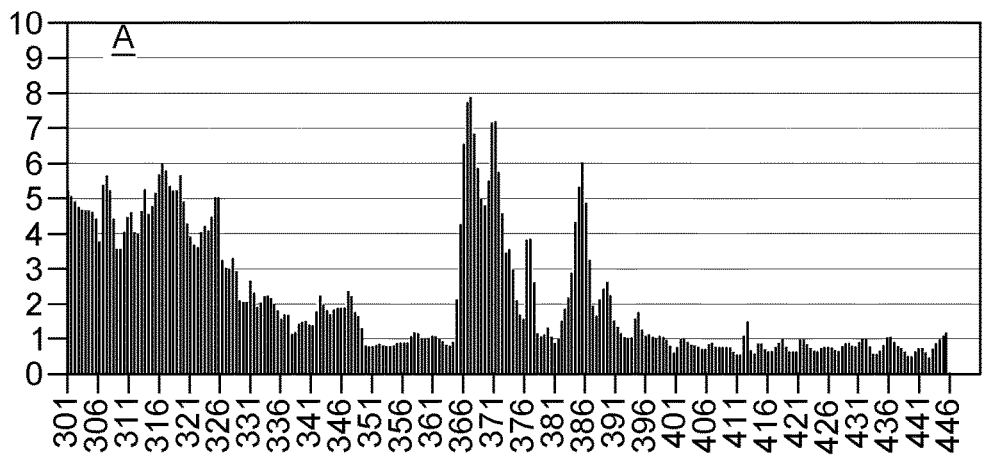
Figure 8C:
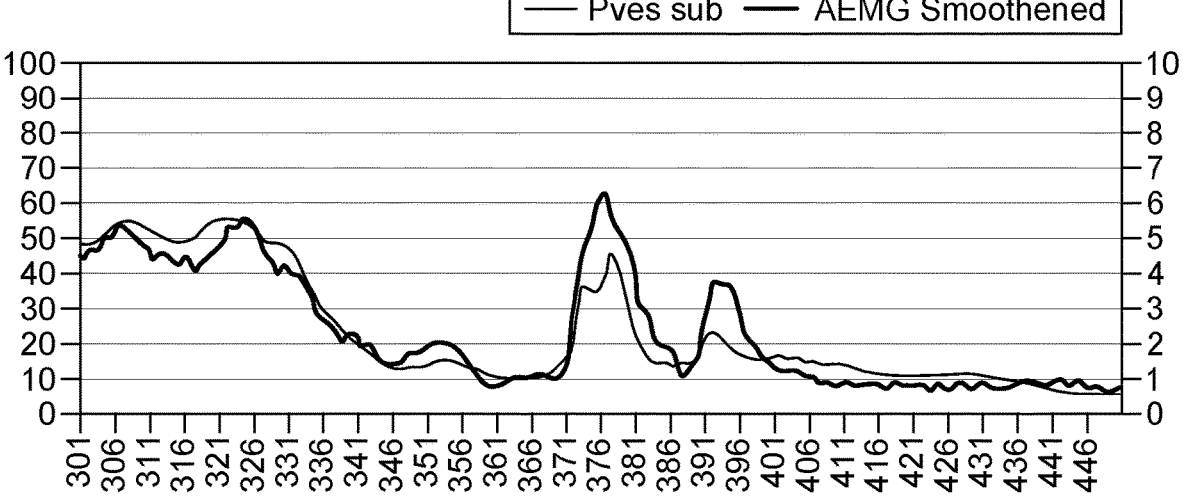

With brief reference to the graphic sequence of FIGS. 6A-C, the zeroed PS data sets are solely depicted, top and middle figure portions, with additive variable data sets depicted bottom figure portion. Via the additive depiction, a relationship for, between and among Pves and AEMG is visibly discernable with reference to the active portion A of the PS data. Again, owing to the contemplated methodology, Pves is exclusively abdominal activity, with the cough/cough/push/cough response appreciated via the illustrated short/short/sustained/short variable responses.

With reference now to each of the graphic sequences of FIGS. 7A-C & 8A-C, the zeroed data sets are shown post filtering, namely, post primary and secondary filtering respectively. Via a bandpass filter or the like, the patient's electrical cardiac activity (i.e., electrocardiogram, a/k/a EKG) is removed from the AEMG signal so as to result in the combined variable plot of FIGS. 7A-C. Via simple averaging filter, with a window of 0.5 sec., the AEMG signal is smoothed. The filtering includes a slight time shift of the AEMG signal to align with the Pves signal as there is a slight time shift in the creation of these signals.

At this point in the comparative assessment of the data sets, the pretest data sets, an analysis may be advantageously, but not necessarily, performed to determine whether the correlation between AEMG and Pves is strong enough. A non-limiting example of correlation determination is to calculate the Pearson Correlation coefficient (r) for the provocative maneuver data sets and to establish an r value for the relationship between the two signals. In such context, an advantageous threshold to determine the strength of the correlation would be an r value >=0.7. The actual r value for this example study was 0.91.

Further at this point in the comparative assessment of the data sets, the pretest data sets, the relationship between AEMG and Pabd is established and thusly Pabd may be generated, fabricated or synthesized from the calibrated AEMG values. For example, and without limitation, the relationship can be a simple one, such as setting a linear relationship between AEMG and Pabd values, based on the provocative maneuvers portion of the acquired data. Such linear relationship may be established using a least squares error estimator, with the formula representing the relation being as simple as:

$$\text{Zeroed Pabd} = 9.9 * \text{Zeroed AEMG}$$

In other circumstances, scenarios, and/or system/method embodiments, the relationship between AEMG and Pabd can be more complicated. An example of a more complicated relationship would be to have a non-linear relationship, or to have a relationship that differs based on the frequency content of either the AEMG signal or Pves signal. This would effectively alter the gain relationship between AEMG and calculated Pabd based on the types of abdominal contractions, e.g., cough compared to push.

Figure 9A:
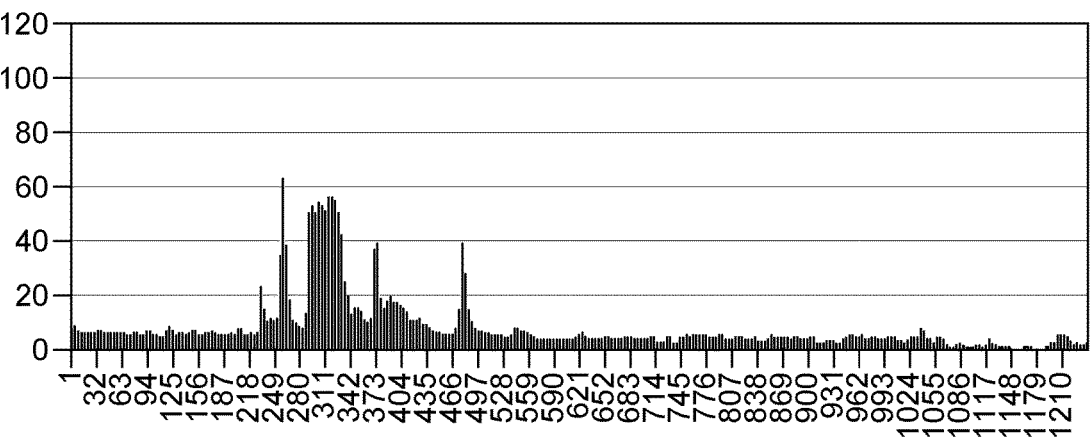
Figure 9A:
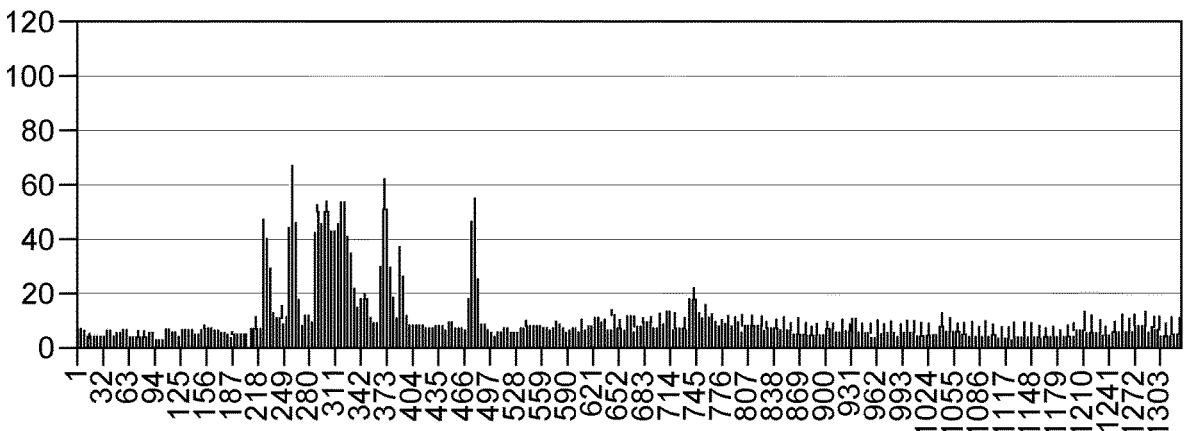
Figure 9A:
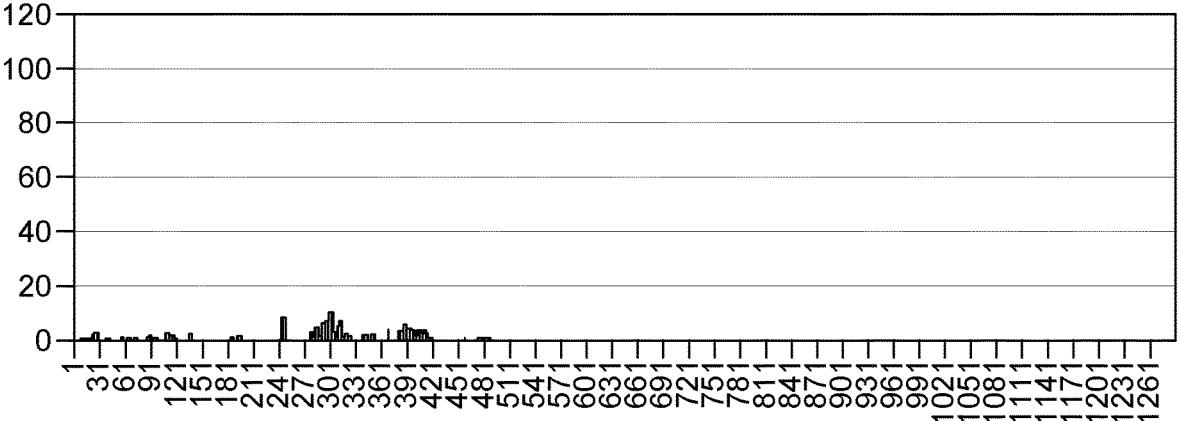
Figure 9B:
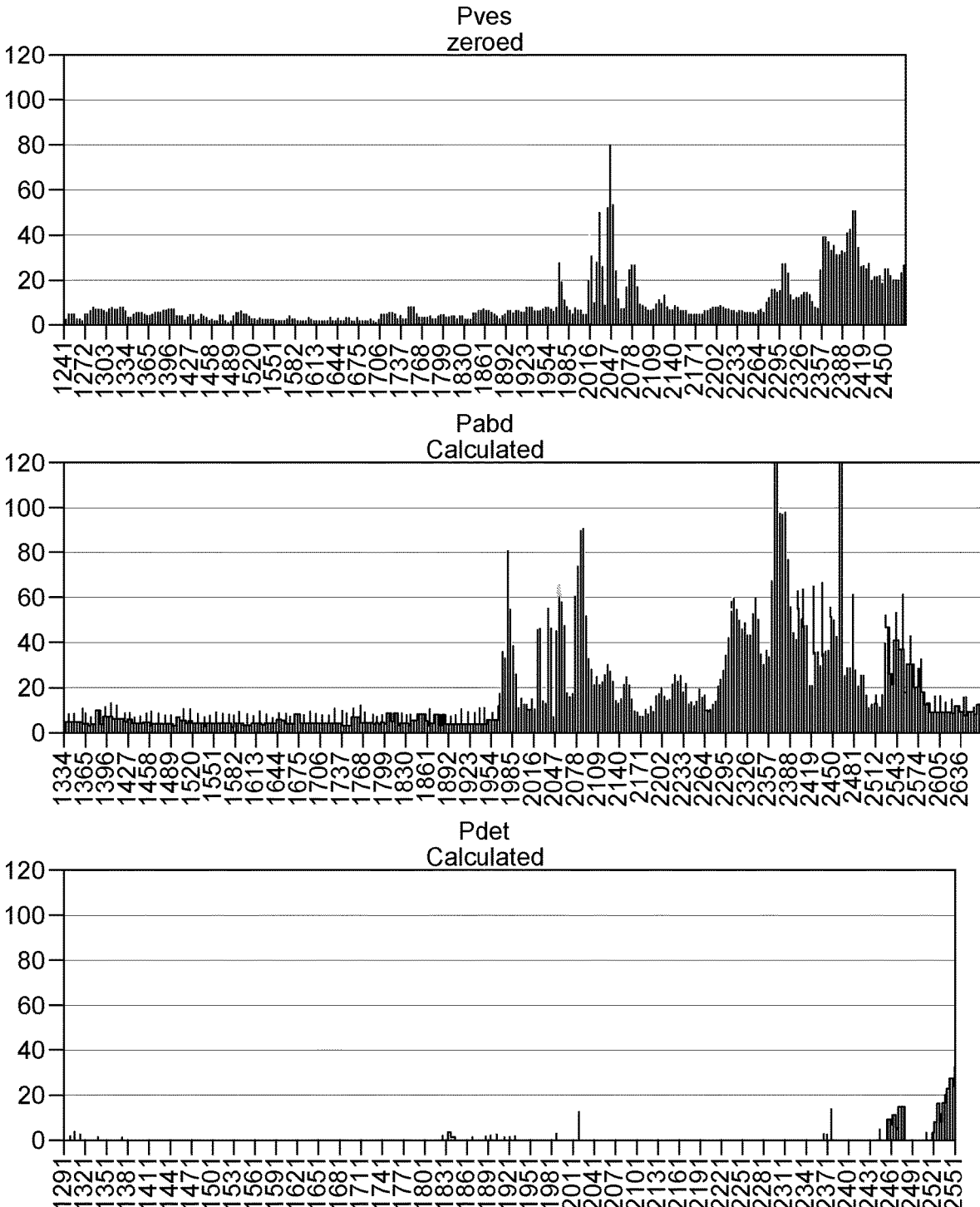
Figure 9C:
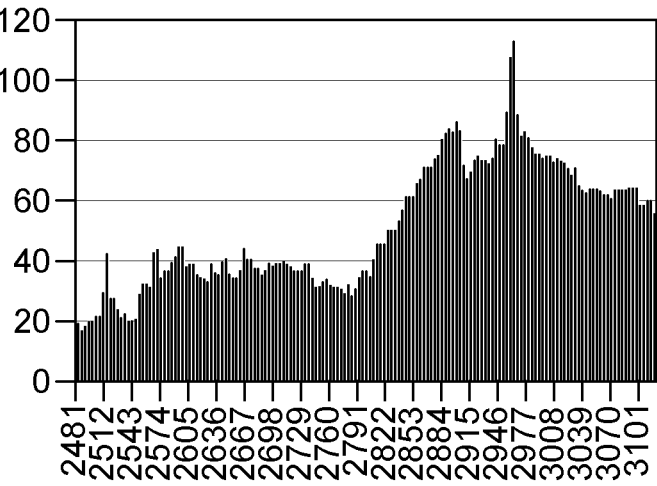
Figure 9C:
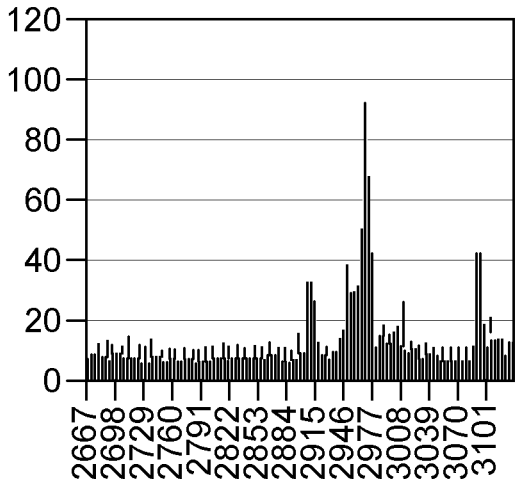
Figure 9C:
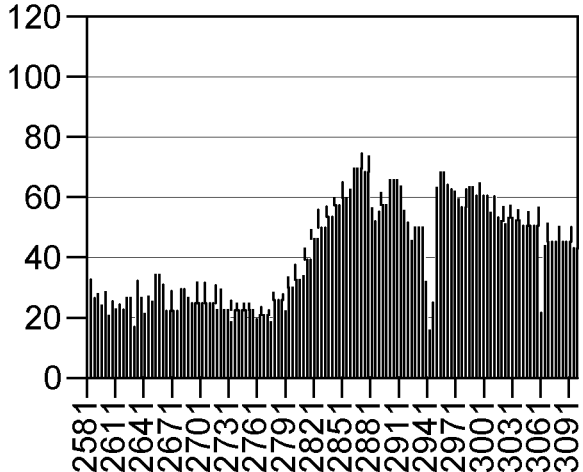

With final reference now to the graphic sequence of FIGS. 9A-C, synthesized Pabd supplants the AEMG value plot heretofore presented, and a resultant derived Pdet value plot is generated. Advantageously, but not necessarily, conventional filtering is contemplated in generating calculated values of Pdet.

What has been described and depicted herein are preferred, non-limiting embodiments of Applicant's subject matter, along with application contexts as the case may be. Since the elements of the methodology and/or system disclosed herein may be embodied in other specific forms without departing from the spirit or general characteristics thereof, some of which forms have been indicated, the embodiments described and depicted herein/with are to be considered in all respects illustrative and not restrictive. Moreover, while nominal operational steps or sequences and/or rubrics/protocols have been set forth, contemplated sequences/protocols are not so limited. Accordingly, the scope of the subject invention is as defined in the language of the appended claims, and includes not insubstantial equivalents thereto.

What is claimed is:

1. A urodynamic study system for generating an abdominal pressure from a measurement of vesical pressure and a measurement of electrical activity of abdominal muscles using electromyography, the system comprising:
    a. a vesical catheter adapted to sense vesical pressure in furtherance of measuring same;
    b. an abdominal electromyography sensor to sense electrical activity of abdominal muscles in furtherance of measuring same; and,
    c. a signal processing interface for producing synchronous channels of vesical pressure and generated abdominal pressure in furtherance of performing a urodynamic patient assessment, the signal processing interface comprising:

i. one or more signal receivers configured to receive first and second signals comprised, respectively, of measured values of vesical pressure and measured values of abdominal electrical activity;

ii. a processer for calibrating select signals from the one or more signal receivers received thereby, select signals from the one or more signal receivers characterized by first measured values of each of vesical pressure and abdominal electrical activity corresponding to a passive patient status characterized by an empty bladder and inactive non-volitional abdominal contractions, and further characterized by one or more measured values of abdominal electrical activity corresponding to one or more active volitional abdominal contractions, said signals associated with measured values of abdominal electrical activity having been filtered for the removal of electrical cardiac activity, resulting calibrated select signals evidencing a relationship between abdominal electrical activity and abdominal pressure in furtherance of obtaining generated abdominal pressure values; and, iii. an output device for outputting synchronous channels of measured values of vesical pressure and generated abdominal pressure correlated to the calibrated select signals.

2. A signal processing interface for producing synchronous channels of vesical pressure and generated abdominal pressure in furtherance of performing a urodynamic patient assessment, the signal processing interface comprising:

a. one or more signal receivers configured to receive first and second signals comprised, respectively, of measured values of vesical pressure and measured values of abdominal electrical activity;

b. a processor for calibrating select signals from the one or more signal receiver received thereby, select signals from the one or more signal receiver modules characterized by first measured values of each of vesical pressure and abdominal electrical activity corresponding to a passive patient status characterized by an empty bladder and inactive non-volitional abdominal contractions, and further characterized by one or more measured values of abdominal electrical activity corresponding to one or more active volitional abdominal contractions, said signals associated with measured values of abdominal electrical activity having been filtered for the removal of electrical cardiac activity, resulting calibrated select signals evidencing a relationship between abdominal electrical activity and abdominal pressure in furtherance of obtaining generated abdominal pressure values; and, c. an output device for outputting synchronous channels of measured values of vesical pressure and generated abdominal pressure correlated to the calibrated select signals.

3. A method of generating abdominal pressure values from measured vesical pressure values and measured abdominal electrical activity using a signal processing interface for producing synchronous channels of vesical pressure and generated abdominal pressure, the interface characterized by, in operative combination, a signal receiving module and a processor for calibrating select signals from the signal receiving module, the method comprising:

a. measuring a quantity of vesical pressure and abdominal electrical activity to obtain first measured values of each of vesical pressure and abdominal electrical activity, said first measured values of each of vesical pressure and abdominal electrical activity corresponding to a passive patient status characterized by an empty bladder and inactive non-volitional abdominal contractions, said first measured values of each of vesical pressure and abdominal electrical activity receivable by the signal receiving module;

b. measuring a quantity of vesical pressure and abdominal electrical activity to obtain second measured values of each of vesical pressure and abdominal electrical activity, said second measured values of each of vesical pressure and abdominal electrical activity corresponding to an active patient status characterized by one or more active volitional abdominal contractions, said second measured values of each of vesical pressure and abdominal electrical activity receivable by the signal receiving module;

c. filtering out electrical cardiac activity from signals associated with measured abdominal electrical activity;

d. calibrating data corresponding to signals associated with first measured values of each of vesical pressure and abdominal electrical activity, and data corresponding to signals associated with second measured values of each of vesical pressure and abdominal electrical activity via the processor; and, e. generating abdominal pressure values from measured values of abdominal electrical activity during a urodynamic study as a result of the calibration of data corresponding to signals associated with first measured values of each of vesical pressure and abdominal electrical activity, and data associated with second measured values of each of vesical pressure and abdominal electrical activity.

4. The method of claim 3 wherein the calibrating includes performing a calibration protocol with regard to said second measured values of vesical pressure and abdominal electrical activity corresponding to an active patient status characterized by one or more active volitional abdominal contractions so as to establish a relationship for and between abdominal electrical activity and abdominal pressure.

5. The method of claim 3 wherein measuring a quantity of vesical pressure is enabled via a vesical catheter.

6. The method of claim 3 wherein measuring a quantity of vesical pressure is enabled via a single vesical catheter.

7. The method of claim 3 wherein measuring a quantity of vesical pressure is enabled with a vesical catheter and measuring a quantity of abdominal electrical activity is enabled via surface electromyography.

8. The method of claim 3 wherein the one or more active volitional abdominal contractions comprise both fast moving and slow moving contractions.

9. The method of claim 3 wherein first and second measured values of each of vesical pressure and abdominal electrical activity are received as signals corresponding to first and second signal receivers of the signal receiving module.

10. The method of claim 3 further comprising determining whether a signal quality of signals associated with measured values of abdominal electrical activity enable generating abdominal pressure values from measured values of abdominal electrical activity during a urodynamic study as a result of the calibration of data associated with first measured values of each of vesical pressure and abdominal electrical activity, and data associated with second measured values of each of vesical pressure and abdominal electrical activity.

* * * * *